United States Patent
Thede et al.

(10) Patent No.: US 8,575,357 B2
(45) Date of Patent: Nov. 5, 2013

(54) SUBSTITUTED (THIAZOLYL-CARBONYL) IMIDAZOLIDINONES AND USE THEREOF

(75) Inventors: Kai Thede, Berlin (DE); Susanne Greschat, Wagenfeld (DE); Kersten Matthias Gericke, Wuppertal (DE); Steffen Wildum, Gerelsberg (DE); Daniela Paulsen, Wuppertal (DE)

(73) Assignee: AiCuris GmbH & Co. KG, Wuppertal (DE)

( * ) Notice: Subject to any disclaimer, the term of this patent is extended or adjusted under 35 U.S.C. 154(b) by 0 days.

(21) Appl. No.: 13/399,969

(22) Filed: Feb. 17, 2012

(65) Prior Publication Data

US 2013/0045999 A1 Feb. 21, 2013

Related U.S. Application Data

(63) Continuation of application No. PCT/EP2010/061923, filed on Aug. 17, 2010.

(30) Foreign Application Priority Data

Aug. 17, 2009 (DE) .......................... 10 2009 038 123

(51) Int. Cl.
A61K 31/427 (2006.01)
C07D 417/06 (2006.01)
(52) U.S. Cl.
USPC .......................................... 548/200; 514/365
(58) Field of Classification Search
USPC ....................................................... 548/200
See application file for complete search history.

(56) References Cited

FOREIGN PATENT DOCUMENTS

| EP | 0 388 909 | 3/1990 |
|---|---|---|
| EP | 0 377 457 | 4/1990 |
| EP | 0 471 991 | 7/1991 |
| WO | WO-02/055079 | 7/2002 |
| WO | WO-03/035076 | 5/2003 |
| WO | WO-03/041711 | 5/2003 |
| WO | WO-03/078413 | 9/2003 |
| WO | WO-2004/058255 | 7/2004 |
| WO | WO-2005/115389 | 12/2005 |
| WO | WO-2006/023462 | 3/2006 |
| WO | WO-2006/062982 | 6/2006 |
| WO | WO-2006/062984 | 6/2006 |
| WO | WO-2010/075962 | 7/2010 |

OTHER PUBLICATIONS

Schickli et al., Human Vaccines, vol. 5, Issue 9, pp. 582-591, Sep. 2009.*
Carpenter et al., "Antiretroviral Therapy in Adults Updated Recommendations of the International AIDS Society—USA Panel," J. Am. Med. Assoc. (2000) 283(3):381-390.
Finzi et al., "Latent Infection of CD4+ T Cells Provides a Mechanism for Lifelong Persistence of HIV-1, Even in Patients on Effective Combination Therapy," Nature Med. (1999) 5(5):512-517.
Flexner, "HIV Drug Development: the Next 25 Years," Nature Reviews Drug Discovery (2007) 6:959-966.
Kavlick et al., "Emergence of Drug-Resistant Human Immunodeficiency Virus Type 1 (HIV-1) Variants and Their Impact on Antiretroviral Therapy of HIV-1 Infection," Antiretroviral Chemotherapy (Edt. De Clercq E.) 2001, ASM Press, 279-312.
Palella, Jr., et al., "Declining Morbidity and Mortality Among Patients with Advanced Human Immunodeficiency Virus Infection," N. Engl. J. Med. (1998) 338(13):853-860.
Ramratnam et al., "The Decay of the Latent Reservoir of Replication-Competent HIV-1 is Inversely Correlated with the Extent of Residual Viral Replication During Prolonged Anti-Retroviral Therapy," Nature Med. (2000) 6(1):82-85.

* cited by examiner

*Primary Examiner* — Laura L. Stockton
(74) *Attorney, Agent, or Firm* — Morrison & Foerster LLP

(57) ABSTRACT

The present invention relates to novel substituted furancarboxamides, methods for their production, their use for the treatment and/or prevention of diseases, as well as their use for the production of medicaments for the treatment and/or prophylaxis of diseases, especially retroviral diseases, in humans and/or animals.

14 Claims, No Drawings

SUBSTITUTED (THIAZOLYL-CARBONYL) IMIDAZOLIDINONES AND USE THEREOF

CROSS REFERENCES TO RELATED APPLICATIONS

This application is a continuation of international patent application PCT/EP2010/061923, filed on Aug. 17, 2010, designating U.S., which international patent application has been published in German language and claims priority from German patent application DE 10 2009 038 123.6, filed on Aug. 17, 2009. The entire contents of these priority applications are incorporated herein by this reference.

BACKGROUND OF THE INVENTION

The present invention relates to novel substituted (thiazolylcarbonyl)imidazolidinones, methods for their preparation, their use for the treatment and/or prophylaxis of diseases, as well as their use for the manufacture of medicaments for the treatment and/or prophylaxis of diseases, especially of retroviral diseases, in humans and/or animals.

HIV (human immunodeficiency virus) causes a chronic persistent progressive infection. The disease proceeds via various stages from the asymptomatic infection to the pathological condition AIDS (acquired immunodeficiency syndrome). AIDS is the final stage of the disease caused by infection. The HIV/AIDS disease is characterized by a long clinical latency period with persistent viraemia which, in the final stage, leads to the failure of the immune defenses.

The introduction of the anti-HIV combination therapy made it possible in the 1990s to effectively slow the down progression of the disease and thus to prolong substantially the life expectancy of HIV-infected patients (Palella, et al., *N. Engl. J. Med.* 1998, 238, 853-860).

The anti-HIV substances currently on the market inhibit the replication of the HI virus by inhibiting the essential viral enzymes reverse transcriptase (RT), protease or integrase, or the entry of HIV into the target cell (review in Flexner, *Nature Reviews Drug Discovery* 2007, 6, 959-966). There are two classes of RT inhibitors: nucleosidic and nucleotidic RT inhibitors (NRTI) act through competitive inhibition or chain termination in the DNA polymerization. Non-nucleosidic RT inhibitors (NNRTI) bind allosterically to a hydrophobic pocket in the vicinity of the active center of the RT and bring about a conformational change in the enzyme. The currently available protease inhibitors (PI) block the active center of the viral protease and thus prevent the maturation of newly produced particles into infectious virions. The only currently authorized integrase inhibitor Raltegravir binds in the active center of the HIV integrase and prevents the integration of the proviral DNA into the host cell genome. Entry inhibitors (fusion inhibitors and coreceptor antagonists) prevent the HIV infection of cells by interacting with the HIV coat protein or by blocking the cellular coreceptors CCR5 or CXCR4.

Since monotherapy with the currently available anti-HIV medicaments leads in a very short time to a failure of the therapy owing to a selection of resistant viruses, usually a combination therapy with several anti-HIV substances from different classes takes place (highly active antiretroviral therapy=HAART; Carpenter, et al., *J. Am. Med. Assoc.* 2000, 283, 381-390).

Despite the advances in antiretroviral chemotherapy, recent investigations show that an eradication of HIV and, associated therewith, a cure of the HIV infection is not to be expected with the available medicaments. The latent virus remains in dormant lymphocytes and represents a reservoir for a reactivation and thus for a renewed spread of the virus (Finzi, et al., *Nature Med.* 1999, 5, 512-517; Ramratnam, et al., *Nature Med.* 2000, 6, 82-85). HIV-infected patients are therefore life-long dependent on an efficient antiviral therapy. Despite combination therapy, a selection of resistant viruses occurs after some time. Since resistance mutations characteristic for each therapeutic class accumulate, the failure of one therapy often means a loss of effect of the complete class of substances. This cross-resistance problem is most pronounced with the class of NNRTIs because in this case a single point mutation in the RT may often be sufficient to bring about a loss of effect of all NNRTIs (review in Kavlick & Mitsuya, *Antiretroviral Chemotherapy* (editor De Clercq E.), 2001, ASM Press, 279-312).

The development of resistances is usually favored by the poor compliance of the patients which is caused by an unfavorable profile of side effects and a complicated dosage regimen for the anti-HIV medicaments.

There is thus a pressing need for novel therapeutic options for controlling an HIV infection. For this purpose, an urgent aim of HIV therapy research is to identify novel chemical lead structures which either address a novel target in the replication of HIV and/or are effective against the growing number of resistant clinical HIV isolates.

EP 377 457 A1 and EP 388 909 A2 describe thiazolecarboxamides having antithrombotic, antiallergic, anti-inflammatory action as well as vasodilatory action and acting as 5-lipooxigenase inhibitors, WO 03/78413 A1, WO 2004/058255 A1 describe thiophenecarboxamides acting on the cannabinoid CB1 receptor, WO 03/041711 A1 describes thiophenecarboxamides as orexin receptor antagonists, WO 2005/115389 A2 describes thiazolecarboxamides for treating a negative energy balance in ruminants, WO 2006/023462 A1 as histamine H3 receptor antagonists, and WO 2006/062984 and WO 2006/062982 A2 as inhibitors of various kinases.

SUMMARY OF THE INVENTION

Against this background, it is an object of the present invention is to provide novel compounds having equal or improved antiviral activity for treating viral infectious diseases in humans and animals, which compounds do not have the disadvantages described above.

Surprisingly, it was found that the substituted (thiazolyl-carbonyl)imidazolidinones described in the present invention have antiviral activity.

The invention relates to compounds of formula

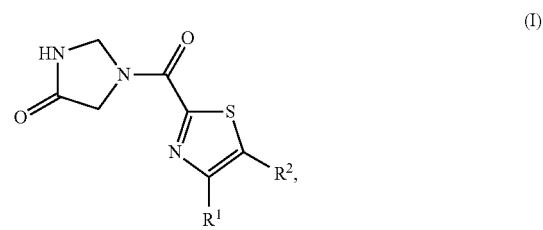

(I)

in which $R^1$ represents phenyl, whereby phenyl is substituted with 1 to 3 substituents, whereby the substituents are selected independently of one another from the group consisting of halogen, hydroxy, cyano, nitro, trifluoromethyl, trifluoromethoxy, trifluoromethylthio, $(C_1-C_4)$-alkyl and $(C_1-C_4)$-alkoxy, wherein $(C_1-C_4)$-alkyl and $(C_1-C_4)$-alkoxy in turn may be substituted one to three times identically or differently with radicals selected from the group consisting of halogen, cyano, hydroxy, $(C_1-C_4)$-alkoxy, amino, mono-$(C_1-C_4)$-alkylamino, di-$(C_1-C_4)$-alkylamino, $(C_3-C_7)$-cycloalkyl and 4- to 7-membered heterocyclyl, whereby the last-mentioned cycloalkyl and heterocyclyl radicals in turn may each be substituted up to three times identically or differently with halogen, cyano, $(C_1-C_4)$-alkyl, trifluoromethyl, hydroxy, $(C_1-C_4)$-alkoxy, trifluoromethoxy, oxo, amino, mono-$(C_1-C_4)$-alkylamino and di-$(C_1-C_4)$-alkylamino, and $R^2$ represents phenyl, whereby phenyl is substituted with 1 to 3 substituents, whereby the substituents are selected independently of one another from the group consisting of halogen, hydroxy, cyano, nitro, trifluoromethyl, trifluoromethoxy, trifluoromethylthio, $(C_1-C_4)$-alkyl and $(C_1-C_4)$-alkoxy, wherein $(C_1-C_4)$-alkyl and $(C_1-C_4)$-alkoxy in turn may be substituted one to three times identically or differently with radicals selected from the group consisting of halogen, cyano, hydroxy, $(C_1-C_4)$-alkoxy, amino, mono-$(C_1-C_4)$-alkylamino, di-$(C_1-C_4)$-alkylamino, $(C_3-C_7)$-cycloalkyl and 4- to 7-membered heterocyclyl, whereby the last-mentioned cycloalkyl and heterocyclyl radicals in turn may each be substituted up to three times identically or differently with halogen, cyano, $(C_1-C_4)$-alkyl, trifluoromethyl, hydroxy, $(C_1-C_4)$-alkoxy, trifluoromethoxy, oxo, amino, mono-$(C_1-C_4)$-alkylamino and di-$(C_1-C_4)$-alkylamino, and the salts thereof, the solvates thereof and the solvates of the salts thereof.

Compounds of the invention are the compounds of formulae (I) and (Ia) and the salts, solvates and solvates of the salts thereof, as well as the compounds which are encompassed by formulae (I) and (Ia) and are mentioned hereinafter as exemplary embodiment(s), and the salts, solvates and solvates of the salts thereof, insofar as the compounds encompassed by formulae (I) and (Ia) and mentioned hereinafter are not already salts, solvates and solvates of the salts.

The compounds of the invention may, depending on their structure, exist in stereoisomeric forms (enantiomers, diastereomers). The invention therefore also encompasses the enantiomers or diastereomers and respective mixtures thereof. The stereoisomerically uniform constituents can be isolated in a known manner from such mixtures of enantiomers and/or diastereomers.

If the compounds of the invention may occur in tautomeric forms, the present invention encompasses all tautomeric forms.

Salts preferred for the purposes of the present invention are physiologically acceptable salts of the compounds of the invention. Also encompassed however are salts which are themselves not suitable for pharmaceutical applications but can be used for example for the isolation or purification of the compounds of the invention.

Physiologically acceptable salts of the compounds of the invention include acid addition salts of mineral acids, carboxylic acids and sulfonic acids, e.g., salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, fumaric acid, maleic acid and benzoic acid.

Physiologically acceptable salts of the compounds of the invention also include salts of usual bases such as, by way of example and preferably, alkali metal salts (e.g. sodium and potassium salts), alkaline earth metal salts (e.g., calcium and magnesium salts) and ammonium salts derived from ammonia or organic amines having 1 to 16 C atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates for the purposes of the invention refer to those forms of the compounds of the invention which in the solid or liquid state form a complex by coordination with solvent molecules. Hydrates are a specific form of solvates in which the coordination takes place with water.

In the context of the present invention, the substituents have the following meaning, unless specified otherwise:

Alkyl and the alkyl moieties in alkoxy and alkoxycarbonyl represent straight-chain or branched alkyl and include, unless indicated otherwise, $(C_1-C_6)$-alkyl, in particular $(C_1-C_4)$-alkyl such as, for example, methyl, ethyl, propyl, isopropyl, butyl, isobutyl.

Alkoxy for the purpose of the invention represents preferably a straight-chain or branched alkoxy radical in particular having 1 to 6, 1 to 4 or 1 to 3 carbon atoms. A straight-chain or branched alkoxy radical having 1 to 3 carbon atoms is preferred. Mention may be made by way of example and preferably of: methoxy, ethoxy, n-propoxy, isopropoxy, t-butoxy, n-pentoxy and n-hexoxy.

Alkoxycarbonyl represents by way of example and preferably methoxycarbonyl, ethoxycarbonyl, n-propoxycarbonyl, isopropoxycarbonyl, t-butoxycarbonyl, n-pentoxycarbonyl and n-hexoxycarbonyl.

Heterocyclyl represents a monocyclic heterocyclic radical having 4 to 7, preferably 5 to 6, ring atoms and up to 3, preferably up to 2, heteroatoms and/or hetero groups from the series N, O, S, SO, $SO_2$, whereby a nitrogen atom can also form an N-oxide. The heterocycle may be saturated or partly unsaturated. Preference is given to 5- to 7-membered monocyclic saturated heterocycles having up to two heteroatoms from the series O, N and S, by way of example and preferably 1,4-oxazepanyl, oxetan-3-yl, pyrrolidin-1-yl, pyrrolidin-2-yl, pyrrolidin-3-yl, tetrahydrofuranyl, tetrahydrothienyl, pyranyl, 1,3-thiazolidinyl, piperidin-1-yl, piperidin-2-yl, piperidin-3-yl, piperidin-4-yl, thiopyranyl, morpholin-2-yl, morpholin-3-yl, morpholin-4-yl, thiomorpholin-2-yl, thiomorpholin-3-yl, thiomorpholin-4-yl, perhydroazepinyl, piperazin-1-yl, piperazin-2-yl.

Halogen represents fluorine, chlorine, bromine or iodine, with preference for fluorine and chlorine, unless indicated otherwise.

Mono-$(C_1-C_4)$-alkylamino for the purpose of the invention represents an amino group having a straight-chain or branched alkyl substituent which comprises 1 to 4 carbon atoms. Mention may be made by way of example and preferably of: methylamino, ethylamino, n-propylamino, isopropylamino, n-butylamino, tert-butylamino, n-pentylamino and n-hexylamino.

Di-($C_1$-$C_4$)-alkylamino for the purpose of the invention represents an amino group having two identical or different straight-chain or branched alkyl substituents which each comprise 1 to 4 carbon atoms. Mention may be made by way of example and preferably of: N,N-dimethylamino, N,N-diethylamino, N-ethyl-N-methylamino, N-methyl-N-n-propylamino, N-isopropyl-N-n-propylamino, N,N-diisopropylamino, N-n-butyl-N-methylamino, N-tert-butyl-N-methylamino, N-methyl-N-n-pentylamino and N-n-hexyl-N-methylamino.

($C_3$-$C_7$)-Cycloalkyl for the purpose of the invention represents a monocyclic saturated carbocycle having 3 to 7 or 3 to 6 ring carbon atoms. Mention may be made by way of example and preferably of: cyclopropyl, cyclobutyl, cyclopentyl, cyclohexyl and cycloheptyl.

The radical definitions listed above and indicated in general or in preferred ranges apply both to the final products of formulae (I) and (Ia) and correspondingly to the starting materials and intermediates required for the preparation in each case.

The radical definitions indicated specifically in the respective combinations or preferred combinations of radicals are replaced irrespective of the particular combinations of radicals indicated as desired also by radical definitions of other combinations.

The invention also relates to compounds of formula (I) in which
$R^1$ represents phenyl,
  whereby phenyl is substituted with 1 to 2 substituents, whereby the substituents are selected independently of one another from the group consisting of halogen, hydroxy, cyano, nitro, trifluoromethyl, trifluoromethoxy, trifluoromethylthio, ($C_1$-$C_4$)-alkyl and ($C_1$-$C_4$)-alkoxy, and
$R^2$ represents phenyl,
  whereby phenyl is substituted with 1 to 2 substituents, whereby the substituents are selected independently of one another from the group consisting of halogen, hydroxy, cyano, nitro, trifluoromethyl, trifluoromethoxy, trifluoromethylthio, ($C_1$-$C_4$)-alkyl and ($C_1$-$C_4$)-alkoxy,
  wherein
    ($C_1$-$C_4$)-alkoxy in turn may be substituted one to three times identically or differently with radicals selected from the group consisting of halogen, cyano, hydroxy, ($C_1$-$C_4$)-alkoxy, amino, mono-($C_1$-$C_4$)-alkylamino, ($C_3$-$C_7$)-cycloalkyl and 4- to 7-membered heterocyclyl,
    whereby the last-mentioned cycloalkyl and heterocyclyl radicals in turn may each be substituted up to three times identically or differently with halogen, cyano, ($C_1$-$C_4$)-alkyl, trifluoromethyl, hydroxy, ($C_1$-$C_4$)-alkoxy, trifluoromethoxy, oxo, amino, mono-($C_1$-$C_4$)-alkylamino and di-($C_1$-$C_4$)-alkylamino,
and the salts thereof, the solvates thereof and the solvates of the salts thereof.

The invention also relates to compounds of formula (I) in which
$R^1$ represents phenyl,
  whereby phenyl is substituted with 1 to 2 substituents, whereby the substituents are selected independently of one another from the group consisting of halogen, cyano, trifluoromethyl, methyl and methoxy, and
$R^2$ represents phenyl,
  whereby phenyl is substituted with 1 to 2 substituents, whereby the substituents are selected independently of one another from the group consisting of halogen, cyano, trifluoromethyl, trifluoromethoxy, methyl and ($C_1$-$C_3$)-alkoxy,
and the salts thereof, the solvates thereof and the solvates of the salts thereof.

The invention also relates to compounds of formula (I) in which
$R^1$ represents phenyl,
  whereby phenyl is substituted with 1 to 2 substituents, whereby the substituents are selected independently of one another from the group consisting of halogen and cyano, and
$R^2$ represents phenyl,
  whereby phenyl is substituted with 1 to 2 substituents, whereby the substituents are selected independently of one another from the group consisting of halogen, cyano and trifluoromethyl,
and the salts thereof, the solvates thereof and the solvates of the salts thereof.

The invention also relates to compounds of formula (I) in which
$R^1$ represents phenyl,
  whereby phenyl is substituted with 1 to 2 substituents, whereby the substituents are selected independently of one another from the group consisting of halogen and cyano, and
$R^2$ represents phenyl,
  whereby phenyl is substituted with 1 to 2 substituents, whereby the substituents are selected independently of one another from the group consisting of halogen and cyano,
and the salts thereof, the solvates thereof and the solvates of the salts thereof.

The invention also relates to compounds of formula

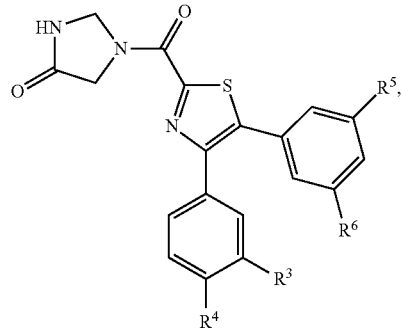

(Ia)

in which
$R^3$ represents halogen or cyano,
$R^4$ represents hydrogen or halogen,
$R^5$ represents halogen, cyano or trifluoromethyl, and
$R^6$ represents hydrogen or halogen,
and the salts thereof, the solvates thereof and the solvates of the salts thereof.

The invention also relates to compounds of formula (Ia) in which
$R^3$ represents halogen or cyano,
$R^4$ represents hydrogen or halogen,
$R^5$ represents halogen or cyano, and
$R^6$ represents hydrogen or halogen,
and the salts thereof, the solvates thereof and the solvates of the salts thereof.

The invention also relates to compounds of formula (Ia) in which
R³ represents fluorine, chlorine or cyano,
R⁴ represents hydrogen, chlorine or fluorine,
R⁵ represents fluorine, chlorine or cyano, and
R⁶ represents hydrogen, chlorine or fluorine,
and the salts thereof, the solvates thereof and the solvates of the salts thereof.

The invention also relates to compounds of formula (Ia) in which
R³ represents chlorine or cyano,
R⁴ represents hydrogen or fluorine,
R⁵ represents halogen or cyano, and
R⁶ represents hydrogen or fluorine,
and the salts thereof, the solvates thereof and the solvates of the salts thereof.

The invention also relates to compounds of formula (Ia) in which
R³ represents chlorine or cyano,
R⁴ represents fluorine,
R⁵ represents chlorine or cyano, and
R⁶ represents fluorine,
and the salts thereof, the solvates thereof and the solvates of the salts thereof.

The invention also relates to compounds of formula (Ia) in which
R³ represents chlorine or cyano,
R⁴ represents fluorine,
R⁵ represents chlorine or cyano, and
R⁶ represents hydrogen,
and the salts thereof, the solvates thereof and the solvates of the salts thereof.

The invention also relates to compounds of formula (Ia) in which
R³ represents chlorine or cyano,
R⁴ represents hydrogen,
R⁵ represents chlorine or cyano, and
R⁶ represents hydrogen,
and the salts thereof, the solvates thereof and the solvates of the salts thereof.

The invention also relates to compounds of formula (Ia) in which
R³ represents chlorine or cyano,
R⁴ represents hydrogen,
R⁵ represents chlorine or cyano, and
R⁶ represents fluorine,
and the salts thereof, the solvates thereof and the solvates of the salts thereof.

The invention furthermore relates to a method for preparing the compounds of formulae (I) and (Ia) whereby compounds of formula

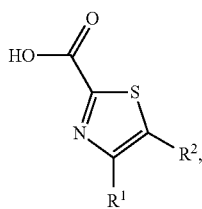

(II)

in which
R¹ and R² have the meaning given above,
are reacted with imidazolidin-4-one or a salt of imidazolidin-4-one.

The reaction generally takes place in inert solvents in the presence of a dehydrating agent, where appropriate in the presence of a base, preferably in a temperature range of from −30° C. to 50° C. under atmospheric pressure.

Examples of inert solvents are halogenated hydrocarbons such as dichloromethane or trichloromethane, hydrocarbons such as benzene or toluene, nitromethane, tetrahydrofuran, 1,4-dioxane, dimethylformamide or acetonitrile. It is also possible to use mixtures of the solvents. Particular preference is given to dichloromethane, dimethylformamide, tetrahydrofuran or toluene.

Bases are, for example, alkali metal carbonates, such as, for example, sodium carbonate or potassium carbonate or sodium bicarbonate or potassium bicarbonate, or organic bases such as trialkylamines, for example triethylamine, N-methylmorpholine, N-methylpiperidine, 4-dimethylaminopyridine or diisopropylethylamine.

Examples for suitable dehydrating agents in this connection are carbodiimides such as, for example, N,N'-diethyl-, N,N'-dipropyl-, N,N'-diisopropyl-, N,N'-dicyclohexylcarbodiimide, N-(3-dimethylaminoisopropyl)-N'-ethylcarbodiimide hydrochloride (EDC), N-cyclohexylcarbodiimide-N'-propyloxymethylpolystyrene (PS-carbodiimide) or carbonyl compounds such as carbonyldiimidazol, or 1,2-oxazolium compounds such as 2-ethyl-5-phenyl-1,2-oxazolium 3-sulfate or 2-tert-butyl-5-methyl-isoxazolium perchlorate, or acylamino compounds such as 2-ethoxy-1-ethoxycarbonyl-1,2-dihydroquinoline, or propanphosphonic anhydride, or isobutyl chloroformate, or bis-(2-oxo-3-oxazolidinyl)phosphoryl chloride, or O-(benzotriazol-1-yl)-N,N,N',N'-tetramethyluroniumhexafluorophosphate (HBTU), 2-(2-oxo-1-(2H)-pyridyl)-1,1,3,3-tetramethyluronium tetrafluoroborate (TPTU) or O-(7-azabenzotriazol-1-yl)-N,N,N',N'-tetramethyluronium hexafluorophosphate (HATU), or 1-hydroxybenzotriazole (HOBt), or benzotriazol-1-yloxytris(dimethylamino)phosphonium hexafluorophosphate (BOP), or benzotriazol-1-yloxytris(pyrrolidino)phosphonium hexafluorophosphate (PyBOP), or N-hydroxysuccinimide, or mixtures of these, with bases.

The condensation is preferably carried out with PyBOP, TBTU or with EDC in the presence of HOBt.

In an alternative method, the compounds of formula (II) can be reacted initially with thionyl chloride and in the second step with compounds of formula R³ or a salt of compounds of formula R³ in the presence of a base such as, for example triethylamine.

The compounds of formulae (I) and (Ia) prepared by the methods described above optionally carry protecting groups which may be removed under conditions known to the person skilled in the art to obtain further compounds of formulae (I) and (Ia).

The compounds of the formula (II) are known or can be prepared by reacting compounds of formula

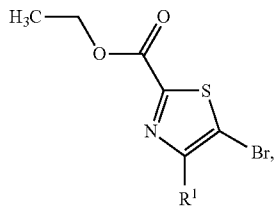

(III)

in which
R¹ has the meaning given above, under Suzuki coupling conditions with compounds of formula $$R^2\text{-}Q \qquad (IV),$$

in which
$R^2$ has the meaning given above and
Q represents —$B(OH)_2$, a boronic acid ester, preferably boronic acid pinacol ester, or —$BF_3^-K^+$.

The Suzuki couplings generally take place in inert solvents, in the presence of a catalyst, where appropriate in the presence of an additional reagent, preferably in a temperature range of from room temperature to 130° C. under atmospheric pressure.

Catalysts are, for example, palladium catalysts customary for Suzuki reaction conditions; preference is given to catalysts such as, for example, dichlorobis(triphenylphosphine)palladium, tetrakistriphenylphosphinepalladium(0), palladium(II) acetate, palladium(II) acetate/tricyclohexylphosphine or bis-(diphenylphosphaneferrocenyl)palladium(II) chloride or palladium(II) acetate with a ligand such as dicyclohexyl[2',4',6-tri(propan-2-yl)biphenyl-2-yl]phosphane.

Examples of additional reagents are potassium acetate, cesium carbonate, potassium carbonate or sodium carbonate, potassium tert-butoxide, cesium fluoride or potassium phosphate; preference is given to additional reagents such as, for example, potassium acetate and/or an aqueous sodium carbonate solution.

Examples of inert solvents are ethers such as dioxane, tetrahydrofuran or 1,2-dimethoxyethane, hydrocarbons such as benzene, xylene or toluene, or carboxamides such as dimethylformamide or dimethylacetamide, alkyl sulfoxides such as dimethyl sulfoxide, or N-methylpyrrolidone, or mixtures of the solvents with alcohols such as methanol or ethanol and/or water; preference is given to 1,2-dimethoxyethane.

In an alternative method, the compounds of the formula (III) can be reacted initially with a compound of the formula (IV) under Suzuki coupling conditions such that the corresponding ester can be isolated. In a second step, this ester can then be converted by hydrolysis with a base into a compound of the formula (II).

The hydrolysis of the ester with a base generally takes place in inert solvents, preferably in a temperature range of from room temperature to the reflux of the solvent at atmospheric pressure.

Bases are, for example, alkali metal hydroxides such as sodium hydroxide, lithium hydroxide or potassium hydroxide, or alkali metal carbonates such as cesium carbonate, sodium carbonate or potassium carbonate; preference is given to lithium hydroxide, potassium hydroxide or sodium hydroxide.

Inert solvents are, for example, halogenated hydrocarbons such as methylene chloride, trichloromethane, carbon tetrachloride, trichloroethane, tetrachloroethane, 1,2-dichloroethane or trichloroethylene, ethers such as diethyl ether, methyl tert-butyl ether, 1,2-dimethoxyethane, 1,4-dioxane, tetrahydrofuran, glycol dimethyl ether or diethylene glycol dimethyl ether, alcohols such as methanol, ethanol, n-propanol, isopropanol, n-butanol or tert-butanol, hydrocarbons such as benzene, xylene, toluene, hexane, cyclohexane or mineral oil fractions, or other solvents such as dimethylformamide, dimethylacetamide, dimethyl sulfoxide, acetonitrile or pyridine, or water, or mixtures of solvents. Preferred solvents are 1,4-dioxane, tetrahydrofuran and/or methanol. Preference is given to lithium hydroxide in tetrahydrofuran/water or 1,4-dioxane/water mixtures or potassium hydroxide in methanol.

The compounds of the formula (IV) are known or can be synthesized by known methods from the corresponding starting materials.

The compounds of the formula (III) are known or can be prepared by brominating compounds of formula

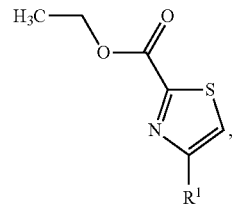

in which
$R^1$ has the meaning given above.

Examples of inert solvents for the bromination are halogenated hydrocarbons such as dichloromethane, trichloromethane, carbon tetrachloride, trichloroethane, tetrachloroethane, 1,2-dichloroethane or trichloroethylene, ethers such as diethyl ether, dioxane, tetrahydrofuran, glycol dimethyl ether or diethylene glycol dimethyl ether, hydrocarbons such as hexane or cyclohexane, organic carboxylic acids such as acetic acid, or other solvents such as ethyl acetate, dimethylformamide or dimethyl sulfoxide. It is also possible to use mixtures of the solvents mentioned. Preference is given to acetic acid, diethyl ether, dioxane, tetrahydrofuran, ethyl acetate, trichloromethane and/or carbon tetrachloride.

Suitable brominating agents are the customary inorganic or organic reagents. These preferably include bromine, N-bromosuccinimide, copper dibromide, pyridine hydrotribromide, dimethylbenzylammonium tribromide or phenyltrimethylammonium tribromide. Particular preference is given to N-bromosuccinamide bromine and copper dibromide.

The bromination is generally carried out in a temperature range of from −20° C. to +150° C., preferably from 0° C. to +80° C. The reaction can be carried out under atmospheric, elevated or reduced pressure (for example from 0.5 to 5 bar). In general, the reaction is carried out under atmospheric pressure.

The compounds of formula (V) are known or can be prepared by reacting compounds of formula

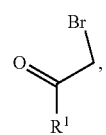

in which
$R^1$ has the meaning given above with ethyl amino(thioxo)acetate.

Inert solvents for this step are, for example, halogenated hydrocarbons, such as dichloromethane, trichloromethane, tetrachloromethane, trichloroethane, tetrachloroethane, 1,2-dichloroethane or trichloroethylene, ethers, such as diethyl ether, dioxane, tetrahydrofuran, glycol dimethyl ether or diethylene glycol dimethyl ether, hydrocarbons, such as hexane or cyclohexane, alcohols, such as methanol or ethanol, or other solvents, such as ethyl acetate, dimethylformamide or dimethyl sulfoxide. It is also possible to use mixtures of the solvents mentioned. Preference is given to ethanol.

The reaction is generally carried out in a temperature range of from −20° C. to +150° C., preferably from 0° C. to +100° C. The reaction can be carried out under atmospheric, elevated or reduced pressure (for example from 0.5 to 5 bar). In general, the reaction is carried out under atmospheric pressure.

The compounds of the formula (VI) are known or can be synthesized by known methods from the corresponding starting materials.

The invention furthermore relates to a method for preparing the compounds of formulae (I) and (Ia) whereby compounds of formula

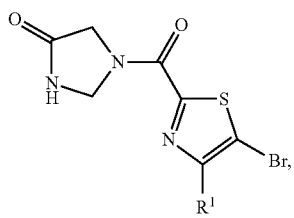

(VII)

in which
R¹ has the meaning given above
are reacted under the Suzuki coupling conditions described above with compounds of formula

R²-Q  (IV), in which
R² has the meaning given above and
Q represents —B(OH)₂, a boronic acid ester, preferably boronic acid pinacol ester, or —BF₃⁻K⁺.

The compounds of formula (VII) are known or can be prepared by reacting compounds of formula

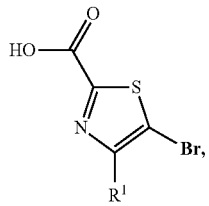

(VIII)

in which
R¹ has the meaning given above
with imidazolidin-4-one or a salt of imidazolidin-4-one, in analogy to the conversion of (II) into (I) or (Ia) described above.

The compounds of formula (VIII) are known or can be prepared by hydrolyzing the ester in compounds of formula

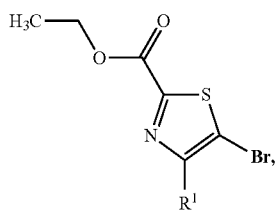

(III)

in which
R¹ has the meaning given above,
using a base, as described above for the alternative method of (III) into (II).

The preparation of the compounds of the invention can be illustrated by the synthesis scheme below.

Synthesis scheme:

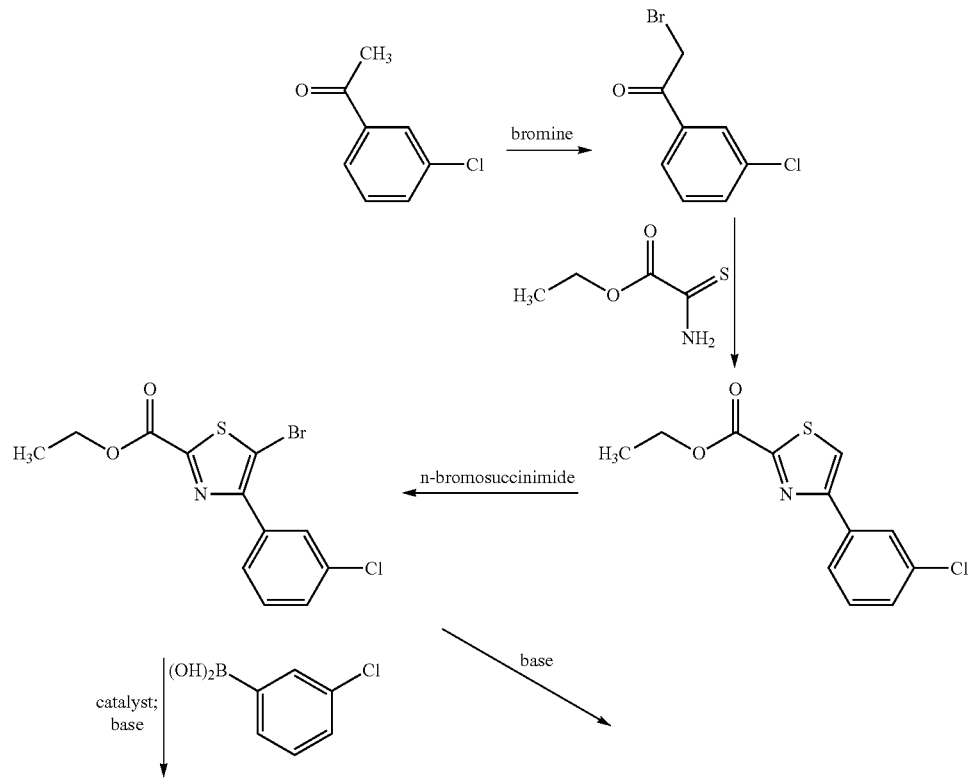

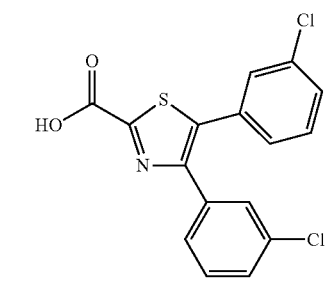
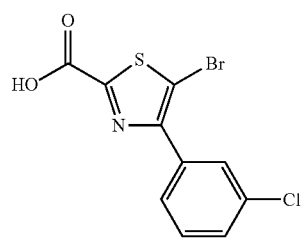
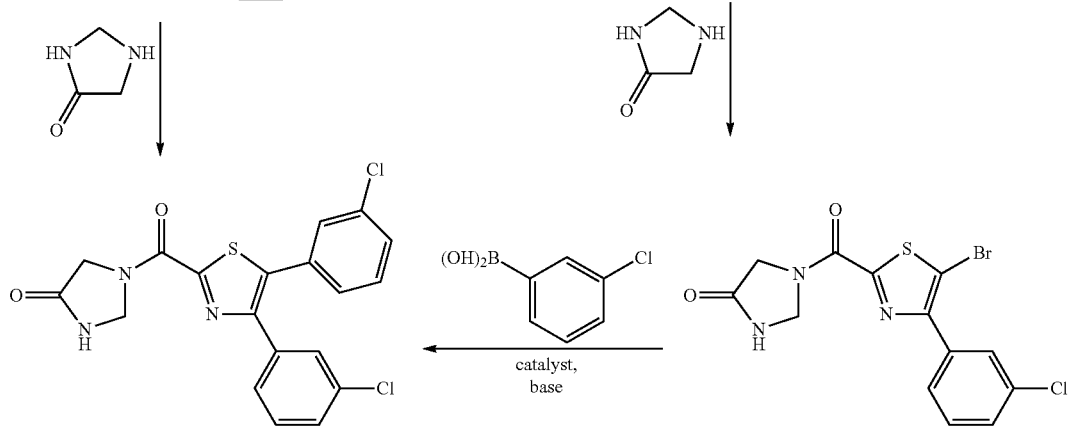

The compounds of the invention show a valuable range of pharmacological effects which could not have been predicted.

They are therefore suitable for use as medicaments for the treatment and/or prophylaxis of diseases in humans and animals.

The compounds of the present invention are distinguished in particular by an advantageous range of antiretroviral effects.

The present invention further relates to the use of the compounds of the invention for the treatment and/or prophylaxis of diseases caused by retroviruses, especially HI viruses.

The present invention further relates to the use of the compounds of the invention for the treatment and/or prophylaxis of diseases, especially of the aforementioned diseases.

The present invention further relates to the use of the compounds of the invention for the manufacture of a medicament for the treatment and/or prophylaxis of diseases, especially of the aforementioned diseases.

The present invention further relates to a method for the treatment and/or prophylaxis of diseases, especially of the aforementioned diseases, using a therapeutically effective amount of the compounds of the invention.

Examples of areas of indication in human medicine which may be mentioned are:

1.) The treatment and prophylaxis of human retroviral infections

2.) The treatment and prophylaxis of infections and diseases (AIDS) caused by HIV-1 (human immunodeficiency virus; formerly called HTLV III/LAV) and HIV-2 and the stages associated therewith, such as ARC (AIDS related complex) and LAS (lymphadenopathy syndrome), as well as the immunodeficiency and encephalopathy caused by this virus.

3.) The treatment of HIV infections caused by mono-, poly- or multiresistant HI viruses.

The expression resistant HI viruses means for example viruses with resistances to nucleosidic RT inhibitors (NRTI), non-nucleosidic RT inhibitors (NNRTI) or protease inhibitors (PI) or viruses with resistances to other principles of action, e.g. T20 (fusion inhibitors).

4.) The treatment or prophylaxis of the AIDS-carrier state.

5.) The treatment or prophylaxis of an HTLV-I or HTLV-II infection.

Examples of indications in veterinary medicine which may be mentioned are:

Infections with a) Maedi-visna (in sheep and goats)
b) progressive pneumonia virus (PPV) (in sheep and goats)
c) caprine arthritis encephalitis virus (in sheep and goats)
d) zwoegerziekte virus (in sheep)
e) infectious anaemia virus (of horses)
f) infections caused by the feline leukaemia virus
g) infections caused by the feline immunodeficiency virus (FIV)
h) infections caused by the simian immunodeficiency virus (SIV)

Preference is given from the area of indications in human medicine to items 2, 3 and 4 detailed above.

The substances are particularly suitable for controlling HI viruses showing resistances to known non-nucleosidic inhibitors of the reverse transcriptase, such as, for example, efavirenz or nevirapine.

The present invention further relates to medicaments comprising at least one compound of the invention and at least one or more further active ingredients, in particular for the treatment and/or prophylaxis of the aforementioned diseases.

The compounds of the invention can also, especially in items 2, 3 and 4 detailed above, advantageously be employed as components of a combination therapy with one or more other compounds which are active in these areas of application. These compounds can for example be employed in combination with effective doses of substances having antiviral activity based on the principles of action detailed below:

HIV protease inhibitors; examples which may be mentioned are: saquinavir, indinavir, ritonavir, nelfinavir, amprenavir, lopinavir, atazanavir, fosamprenavir, tipranavir, darunavir;

nucleosidic, nucleotidic and non-nucleosidic inhibitors of the HIV reverse transcriptase; examples which may be mentioned are: zidovudine, lamivudine, didanosine, zalcitabine, stavudine, lamivudine, abacavir, tenofovir, adefovir, emtricitabine, amdoxovir, apricitabine, racivir, nevirapine, delavirdine, efavirenz, etravirine, rilpivirine, UK-453,061;

HIV integrase inhibitors, examples which may be mentioned are: raltegravir, elvitegravir;

HIV fusion inhibitors; an example which may be mentioned is: enfuvirtide; inhibitors of the CXCR4/CCR5/gp120 interaction; examples which may be mentioned are: maraviroc, vicriviroc, INCB009471, AMD-070;

inhibitors of the polyprotein maturation; an example which may be mentioned is: bevirimat.

This selection is intended to serve to illustrate the possible combinations but not to restrict to the examples detailed here. In principle, every combination of the compounds of the invention with substances having antiviral activity is to be considered as within the scope of the invention.

The compounds of the invention may act systemically and/or locally. They can for this purpose be administered in a suitable way, such as, for example, orally, parenterally, pulmonarily, nasally, sublingually, lingually, buccally, rectally, dermally, transdermally, conjunctivally, otically or as an implant or stent.

For these administration routes the compounds of the invention can be administered in suitable administration forms.

Suitable for oral administration are administration forms which function according to the prior art and deliver the compounds of the invention rapidly and/or in a modified manner, and which contain the compounds of the invention in crystalline and/or amorphized and/or dissolved form, such as, for example, tablets (uncoated or coated tablets, for example having coatings which are resistant to gastric juice or dissolve with a delay or are insoluble and control the release of the compound of the invention), tablets or films/wafers which disintegrate rapidly in the oral cavity, films/lyophilizates, capsules (for example hard or soft gelatin capsules), sugar-coated tablets, granules, pellets, powders, emulsions, suspensions, aerosols or solutions.

Parenteral administration can take place with avoidance of an absorption step (e.g. intravenous, intraarterial, intracardiac, intraspinal or intralumbar) or with inclusion of an absorption (e.g. intramuscular, subcutaneous, intracutaneous, percutaneous, or intraperitoneal). Administration forms suitable for parenteral administration are, inter alia, preparations for injection and infusion in the form of solutions, suspensions, emulsions, lyophilizates or sterile powders.

Suitable for the other administration a routes are, for example, pharmaceutical forms for inhalation (inter alia powder inhalers, nebulizers), nasal drops, solutions, sprays; tablets, films/wafers or capsules, for lingual, sublingual or buccal administration, suppositories, preparations for ears or eyes, vaginal capsules, aqueous suspensions (lotions, shaking mixtures), lipophilic suspensions, ointments, creams, transdermal therapeutic systems (such as for example patches), milk, pastes, foams, dusting powders, implants or stents.

The compounds of the invention can be converted into the stated administration forms. This can take place in a manner known per se by mixing with inert, non-toxic, pharmaceutically acceptable excipients. These excipients include inter alia carriers (for example microcrystalline cellulose, lactose, mannitol), solvents (e.g. liquid polyethylene glycols), emulsifiers and dispersants or wetting agents (for example sodium dodecyl sulfate, polyoxysorbitan oleate), binders (for example polyvinylpyrrolidone), synthetic and natural polymers (for example albumin), stabilizers (e.g. antioxidants such as, for example, ascorbic acid), colors (e.g. inorganic pigments such as, for example, iron oxides) and taste and/or odor corrigents.

The present invention further relates to medicaments which comprise at least one compound of the invention, usually together with one or more inert, non-toxic, pharmaceutically acceptable excipients, as well as to their use for the aforementioned purposes.

It has generally proved to be advantageous both in human and in veterinary medicine to administer the active ingredient(s) of the invention in total amounts of from 0.1 to 200 mg/kg, preferably 1 to 100 mg/kg, of body weight every 24 hours, where appropriate in the form of a plurality of single doses, to achieve the desired result. A single dose preferably comprises the active ingredient(s) in amounts of from 1 to 80 mg/kg, in particular 1 to 30 mg/kg, of body weight.

It may nevertheless be necessary where appropriate to deviate from the stated amounts, in particular as a function of body weight, administration route, individual response to the active ingredient, type of preparation and time or interval over which administration takes place. Thus, in some cases it may be sufficient to make do with less than the aforementioned minimum amount, whereas in other cases the upper limit mentioned must be exceeded. In the case of an administration of larger amounts, it may be advisable to distribute these in a plurality of single doses over the day.

The percentage data in the following tests and examples are, unless indicated otherwise, percentages by weight; parts are parts by weight. Solvent ratios, dilution ratios and concentration data of liquid/liquid solutions are based in each case on volume. The statement "w/v" means "weight/volume". Thus, for example, "10% w/v" means: 100 ml of solution or suspension contain 10 g of substance.

DESCRIPTION OF PREFERRED EMBODIMENTS

A) Examples

Abbreviations:
aq. aqueous; aqueous solution
DCI direct chemical ionization (in MS)
DMA N,N-dimethylacetamide
DME 1,2-dimethoxyethane
DMF N,N-dimethylformamide
DMSO dimethyl sulfoxide
EDC N'-(3-dimethylaminopropyl)-N-ethylcarbodiimide×HCl
eq. equivalent(s)
ESI electrospray ionization (in MS)
h hour(s)
HATU O-(7-azabenzotriazol-1-yl)-N,N,N',N'-tetramethyluronium hexafluorophosphate
HPLC high-performance/high-pressure liquid chromatography
conc. concentrated
LC-MS liquid chromatography-coupled mass spectroscopy
min minute(s)
MS mass spectroscopy
NMR nuclear magnetic resonance spectroscopy PyBOP Benzotriazol-1-yloxytris(pyrrolidino)phosphonium hexafluorophosphate
$R_t$ retention time (in HPLC)
RT room temperature
TBTU O-(benzotriazol-1-yl)-N,N,N',N'-tetramethyluronium tetrafluoroborate
TFA trifluoroacetic acid
THF tetrahydrofuran
TMOF trimethyl orthoformate LC-MS/GC-MS Methods:

Method 1:
MS instrument type: Micromass ZQ; HPLC instrument type: HP 1100 Series; UV, DAD; column: Phenomenex Gemini 3μ 30 mm×3.00 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 210 nm.

Method 2:
Instrument: Micromass Quattro LCZ with HPLC Agilent Series 1100; column: Phenomenex Synergi 2μ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 208-400 nm.

Method 3:
MS instrument type: Micromass ZQ; HPLC instrument type: Waters Alliance 2795; column: Phenomenex Synergi 2μ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.

Method 4:
Instrument: Micromass Quattro LCZ with HPLC Agilent Serie 1100; column: Phenomenex Onyx Monolithic C18, 100 mm×3 mm; eluent A: 1 l of water+0.5 ml of 50% formic acid, eluent B: 1 l of acetonitrile+0.5 ml of 50% formic acid; gradient: 0.0 min 90% A→2 min 65% A→4.5 mm 5% A→6 min 5% A; flow rate: 2 ml/min; oven: 40° C.; UV detection: 208-400 nm.

Method 5:
Instrument: Micromass Quattro Premier with Waters HPLC Acquity; column: Thermo Hypersil GOLD 1.9μ 50 mm×1 mm; eluent A: 1 l of water+0.5 ml of 50% formic acid, eluent B: 1 l of acetonitrile+0.5 ml of 50% formic acid; gradient: 0.0 min 90% A→0.1 min 90% A→1.5 min 10% A→2.2 min 10% A; oven: 50° C.; flow rate: 0.33 ml/min; UV detection: 210 nm.

Method 6:
MS instrument type: Waters ZQ; HPLC instrument type: Waters Alliance 2795; column: Phenomenex Onyx Monolithic C18, 100 mm×3 mm; eluent A: 1 l of water+0.5 ml of 50% formic acid, eluent B: 1 l of acetonitrile+0.5 ml of 50% formic acid; gradient: 0.0 min 90% A→4.2 min 65% A→4.5 min 5% A→6 min 5% A; flow rate: 2 ml/min; oven: 40° C.; UV detection: 210 nm.

Method 7:
MS instrument type: Micromass ZQ; HPLC instrument type: Waters Alliance 2795; column: Phenomenex Synergi 2.5μ MAX-RP 100A Mercury 20 mm×4 mm; eluent A: 1 l of water+0.5 ml of 50% formic acid, eluent B: 1 l of acetonitrile+0.5 ml of 50% formic acid; gradient: 0.0 min 90% A→0.1 min 90% A→3.0 min 5% A→4.0 min 5% A→4.01 min 90% A; flow rate: 2 ml/min; oven: 50° C.; UV detection: 210 nm.

Method 8:
Instrument: Micromass Quattro LCZ with HPLC Agilent Series 1100; column: Phenomenex Gemini 3μ 30 mm×3.00 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 208-400 nm.

Method 9:
Instrument: Micromass Quattro LCZ with HPLC Agilent Series 1100; column: Phenomenex Synergi 2.5μ MAX-RP 100A Mercury 20 mm×4 mm; eluent A: 1 l of water+0.5 ml of 50% formic acid, eluent B: 1 l of acetonitrile+0.5 ml of 50% formic acid; gradient: 0.0 min 90% A→0.1 min 90% A→3.0 min 5% A→4.0 min 5% A→4.1 min 90% A; flow rate: 2 ml/min; oven: 50° C.; UV detection: 208-400 nm.

Method 10:
MS instrument type: Waters (Micromass) Quattro Micro; HPLC instrument type: Agilent 1100 Series; column: Thermo Hypersil GOLD 3μ 20 mm×4 mm; eluent A: 1 l of water+0.5 ml of 50% formic acid, eluent B: 1 l of acetonitrile+0.5 ml of 50% formic acid; gradient: 0.0 min 100% A 3.0 min 10% A→4.0 min 10% A→4.01 min 100% A (flow rate 2.5 ml)→5.00 min 100% A; oven: 50° C.; flow rate: 2 ml/min; UV detection: 210 nm.

Method 11:
Instrument: Micromass GCT, GC6890; column: Restek RTX-35, 15 m×200 μm×0.33 μm; constant helium flow: 0.88 ml/min; oven: 70° C.; inlet: 250° C.; gradient: 70° C., 30° C./min→310° C. (maintained for 3 min).

Method 12:
Instrument: Waters ACQUITY SQD HPLC System; column: Waters Acquity UPLC HSS T3 1.8μ 50×1 mm; eluent A: 1 l of water+0.25 ml of 99% formic acid, eluent B: 1 l of acetonitrile+0.25 ml of 99% formic acid; gradient: 0.0 min 90% A→1.2 min 5% A→2.0 min 5% A oven: 50° C.; flow rate: 0.40 ml/min; UV detection: 210-400 nm.

Starting Materials and Intermediates:

Example 1A

2-Bromo-1-(3-chloro-4-fluorophenyl)ethanone

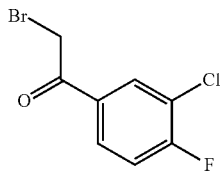 [SMILES: O=C(CBr)c1ccc(F)c(Cl)c1]

At 0° C., 1.00 g (5.79 mmol) of 3-chloro-4-fluoroacetophenone is provided in 20 ml of a 1:1 mixture of 1,4-dioxane and diethyl ether, a solution of 0.30 ml (5.79 mmol) of bromine in 10 ml of a 1:1 mixture of 1,4-dioxane and diethyl ether is added dropwise with exclusion of light and the mixture is stirred for 4 hours. Water and dichloromethane are subsequently added, the phases are separated, the aqueous phase is extracted with dichloromethane and, the combined organic phases are dried over sodium sulfate, filtered and concentrated. 1.35 g (63% of theory) of the title compound having a purity of 68% are obtained which are reacted without further purification.

$^1$H-NMR (400 MHz, DMSO-$d_6$): δ=8.23 (dd, 1H), 8.04 (ddd, 1H), 7.63 (t, 1H), 4.97 (s, 2H). GC-MS (Method 11): $R_t$=5.22 min; MS (EIpos): m/z=252 [M]$^+$.

Example 2A

Ethyl 4-(3-chloro-4-fluorophenyl)-1,3-thiazole-2-carboxylate

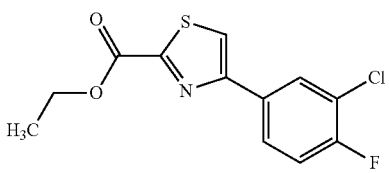 [SMILES: CCOC(=O)c1nc(-c2ccc(F)c(Cl)c2)cs1]

1.35 g of the compound from Example 1A having a purity of 68% (5.37 mmol) are heated under reflux in 25 ml of ethanol, a solution of 0.72 g (5.37 mmol) of ethyl amino(thioxo)acetate and 10 ml of ethanol is added dropwise and the mixture is heated under reflux for 18 hours. The reaction mixture is concentrated and the residue is purified by flash chromatography (mobile phase: cyclohexane/ethyl acetate 10:1), and 1.94 g of the title compound having a purity of 57% (100% of theory) are obtained.

$^1$H-NMR (400 MHz, DMSO-$d_6$): δ=8.65 (s, 1H), 8.21 (dd, 1H), 8.03 (ddd, 1H), 7.55 (t, 1H), 4.42 (q, 2H), 1.36 (t, 3H).

LC-MS (Method 5): $R_t$=1.15 min; MS (ESIpos): m/z=258 [M+H]$^+$.

Example 3A

Ethyl 4-(3-chlorophenyl)-1,3-thiazole-2-carboxylate

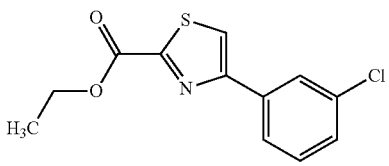 [SMILES: CCOC(=O)c1nc(-c2cccc(Cl)c2)cs1]

The preparation of the title compound takes place in analogy to the synthesis of the compound from Example 2A starting with 2-bromo-1-(3-chlorophenyl)ethanone. 1.51 g (73% of theory) of the title compound are obtained.

$^1$H-NMR (400 MHz, DMSO-$d_6$): δ=8.68 (s, 1H), 8.07 (t, 1H), 7.99 (d, 1H), 7.53 (t, 1H), 7.48 (d, 1H), 4.43 (q, 2H), 1.37 (t, 3H).

LC-MS (Method 1): $R_t$=2.69 min; MS (ESIpos): m/z=268 [M+H]$^+$.

Example 4A

Ethyl 5-bromo-4-(3-chloro-4-fluorophenyl)-1,3-thiazole-2-carboxylate

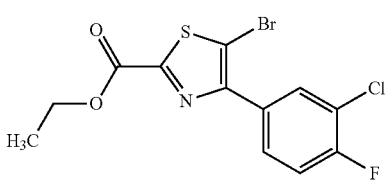 [SMILES: CCOC(=O)c1nc(-c2ccc(F)c(Cl)c2)c(Br)s1]

1.94 g of the compound from Example 2A having a purity of 57% (3.87 mmol) are provided in 35 ml of dichloromethane, 6.04 g (33.9 mmol) of N-bromosuccinimide and a spatula tip of iron trichloride are added and the mixture is heated under reflux for 18 hours. The reaction mixture is concentrated, the residue is purified by flash chromatography (mobile phase: cyclohexane/ethyl acetate 30:1), and 1.30 g (83% of theory) of the title compound are obtained.

$^1$H-NMR (400 MHz, DMSO-$d_6$): δ=8.04 (dd, 1H), 7.90 (ddd, 1H), 7.61 (t, 1H), 4.42 (q, 2H), 1.35 (t, 3H).

LC-MS (Method 5): $R_t$=1.52 min; MS (ESIpos): m/z=364 [M+H]$^+$.

Example 5A

Ethyl 5-bromo-4-(3-chlorophenyl)-1,3-thiazole-2-carboxylate

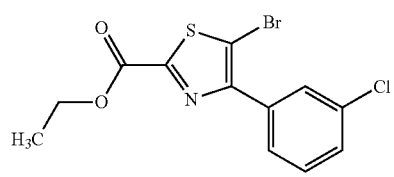 [SMILES: CCOC(=O)c1nc(-c2cccc(Cl)c2)c(Br)s1]

The preparation of the title compound takes place in analogy to the synthesis of the compound from Example 4A starting with the compound of Example 3A. 1.95 g of the title compound having a purity of 65% (98% of theory) are obtained.

LC-MS (Method 1): $R_t$=3.01 min; MS (ESIpos): m/z=346 [M+H]$^+$.

Example 6A

5-Bromo-4-(3-chloro-4-fluorophenyl)-1,3-thiazole-2-carboxylic acid

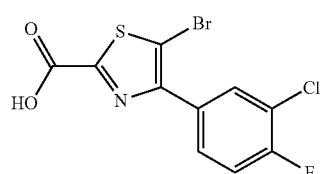

400 mg (1.10 mmol) of the compound from Example 4A are provided in 19 ml of tetrahydrofuran, and 263 mg (11.0 mmol) of lithium hydroxide and 19 ml of water are added at room temperature. The mixture is stirred at room temperature overnight, a 1N aqueous hydrogen chloride solution is then added until an acidic pH is achieved, the mixture is extracted with ethyl acetate and the organic phase is washed with water, dried over sodium sulfate, filtered and concentrated. 190 mg of the title compound having a purity of 86% (44% of theory) are obtained.

LC-MS (Method 1): $R_t$=2.77 min; MS (ESIpos): m/z=336 [M+H]$^+$.

Example 7A

1-{[5-Bromo-4-(3-chloro-4-fluorophenyl)-1,3-thiazole-2-yl]carbonyl}imidazolidin-4-one

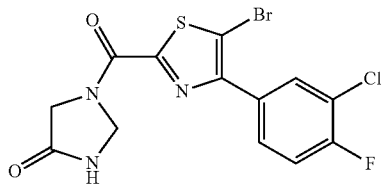 [SMILES: O=C1CN(C(=O)c2nc(-c3ccc(F)c(Cl)c3)c(Br)s2)CN1]

190 mg of the compound from Example 6A having a purity of 86% (0.49 mmol), 107 mg (0.54 mmol) of the compound from Example 20A and 380 mg (0.73 mmol) of PyBOP are provided in 2 ml of tetrahydrofuran, and 0.27 ml (1.56 mmol) of N,N-diisopropylethylamine are added at room temperature. The reaction mixture is stirred at room temperature overnight and then purified by preparative HPLC (RP18 column; mobile phase: acetonitrile/water gradient with the addition of 0.1% formic acid). 109 mg (55% of theory) of the title compound are obtained.

$^1$H-NMR (400 MHz, DMSO-$d_6$): δ=8.80 (s, 0.6H), 8.71 (s, 0.4H), 8.16-8.09 (m, 1H), 8.01-7.93 (m, 1H), 7.66-7.59 (m, 1H), 5.45 (s, 0.8H), 4.91 (s, 1.2H), 4.55 (s, 1.2H), 4.00 (s, 0.8H).

LC-MS (Method 7): $R_t$=1.86 min; MS (ESIpos): m/z=404 [M+H]$^+$.

Example 8A 4-(3-Chloro-4-fluorophenyl)-5-(3-chloro-5-fluorophenyl)-1,3-thiazole-2-carboxylic acid

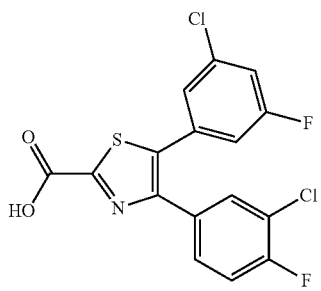 [SMILES: O=C(O)c1nc(-c2ccc(F)c(Cl)c2)c(-c2cc(F)cc(Cl)c2)s1]

Under argon, 100 mg (0.27 mmol) of the compound from Example 4A are provided in 4 ml of 1,2-dimethoxyethane, and 71.7 mg (0.41 mmol) of 3-chloro-5-fluorophenylboronic acid, 1.5 ml (1.37 mmol) of an aqueous sodium bicarbonate solution (10%) and 9.5 mg (8 μmol) of tetrakis(triphenylphosphine)palladium(0) are added. The mixture is stirred at 80° C. overnight. The mixture is concentrated and the residue is purified by preparative HPLC (RP18 column; mobile phase: acetonitrile/water gradient), and 93.0 mg (88% of theory) of the title compound are obtained.

$^1$H-NMR (400 MHz, DMSO-$d_6$): δ=7.67 (dd, 1H), 7.48 (dt, 1H), 7.38 (t, 1H), 7.31 (ddd, 1H), 7.28 (t, 1H), 7.23 (ddd, 1H).

LC-MS (Method 1): $R_t$=3.57 min; MS (ESIpos): m/z=386 [M+H]$^+$.

Example 9A 4-(3-Chloro-4-fluorophenyl)-5-(3-chlorophenyl)-1,3-thiazole-2-carboxylic acid

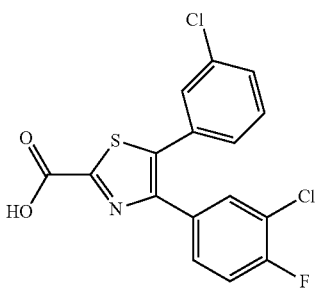 [SMILES: O=C(O)c1nc(-c2ccc(F)c(Cl)c2)c(-c2cccc(Cl)c2)s1]

The preparation of the title compound takes place in analogy to the synthesis of the compound from Example 8A starting with the compound from Example 4A. 80.0 mg (79% of theory) of the title compound are obtained.

$^1$H-NMR (400 MHz, DMSO-$d_6$): δ=7.65 (dd, 1H), 7.48-7.28 (m, 6H).

LC-MS (Method 7): $R_t$=2.14 min; MS (ESIpos): m/z=368 [M+H]$^+$.

Example 10A 5-(3-Chloro-5-fluorophenyl)-4-(3-chlorophenyl)-1,3-thiazole-2-carboxylic acid

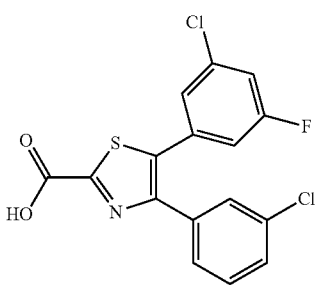 [SMILES: O=C(O)c1nc(-c2cccc(Cl)c2)c(-c2cc(F)cc(Cl)c2)s1]

The preparation of the title compound takes place in analogy to the synthesis of the compound from Example 8A starting with the compound from Example 5A. 83.0 mg (78% of theory) of the title compound are obtained.

$^1$H-NMR (400 MHz, DMSO-$d_6$): δ=7.55-7.53 (m, 1H), 7.48 (dt, 1H), 7.39-7.33 (m, 2H), 7.30-7.24 (m, 2H), 7.24-7.19 (m, 1H).

LC-MS (Method 1): $R_t$=3.33 min; MS (ESIpos): m/z=368 [M+H]$^+$.

Example 11A 5-(3-Chloro-4-fluorophenyl)-4-(3-chlorophenyl)-1,3-thiazole-2-carboxylic acid

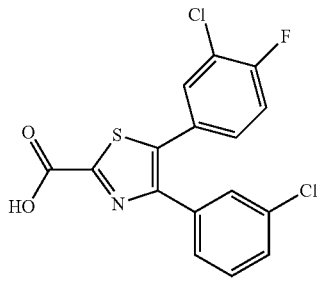 [SMILES: O=C(O)c1nc(-c2cccc(Cl)c2)c(-c2ccc(F)c(Cl)c2)s1]

The preparation of the title compound takes place in analogy to the synthesis of the compound from Example 8A starting with the compound from Example 5A. 59.0 mg (56% of theory) of the title compound are obtained.

$^1$H-NMR (400 MHz, DMSO-$d_6$): δ=7.58 (dd, 1H), 7.55-7.52 (m, 1H), 7.45 (t, 1H), 7.36-7.30 (m, 3H), 7.26 (dt, 1H).

LC-MS (Method 1): $R_t$=3.26 min; MS (ESIpos): m/z=368 [M+H]$^+$.

Example 12A 4-(3-Chlorophenyl)-5-(3-cyano-4-fluorophenyl)-1,3-thiazole-2-carboxylic acid

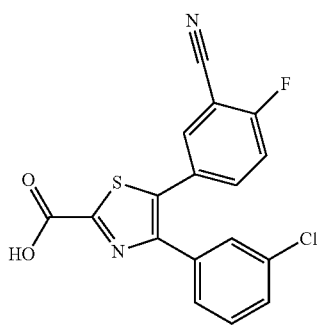 [SMILES: N#Cc1cc(-c2sc(C(=O)O)nc2-c2cccc(Cl)c2)ccc1F]

The preparation of the title compound takes place in analogy to the synthesis of the compound from Example 8A starting with the compound from Example 5A. 42.4 mg (57% of theory) of the title compound are obtained.

LC-MS (Method 7): $R_t$=2.23 min; MS (ESIpos): m/z=359 [M+H]$^+$.

Example 13A 4-(3-Chlorophenyl)-5-(3-cyanophenyl)-1,3-thiazole-2-carboxylic acid

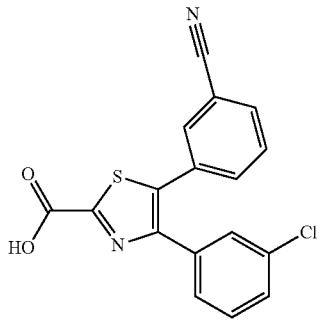 [SMILES: N#Cc1cccc(-c2sc(C(=O)O)nc2-c2cccc(Cl)c2)c1]

The preparation of the title compound takes place in analogy to the synthesis of the compound from Example 8A starting with the compound from Example 5A. 556 mg of the title compound having a purity of 41% (46% of theory) are obtained.

LC-MS (Method 10): $R_t$=2.13 min; MS (ESIpos): m/z=341 [M+H]$^+$.

Example 14A 4-(3-Chlorophenyl)-5-[3-(trifluoromethyl)phenyl]-1,3-thiazole-2-carboxylic acid

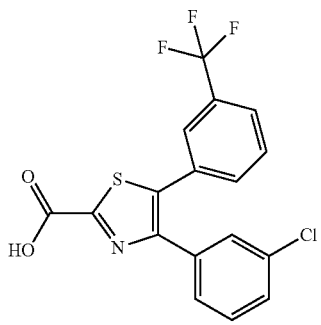 [SMILES: O=C(O)c1nc(-c2cccc(Cl)c2)c(-c2cccc(C(F)(F)F)c2)s1]

The preparation of the title compound takes place in analogy to the synthesis of the compound from Example 8A starting with the compound from Example 5A. 246 mg of the title compound having a purity of 64% (55% of theory) are obtained.

LC-MS (Method 5): $R_t$=1.27 min; MS (ESIpos): m/z=384 [M+H]$^+$.

Example 15A 4-(3-Chloro-4-fluorophenyl)-5-(3-cyano-4-fluorophenyl)-1,3-thiazole-2-carboxylic acid

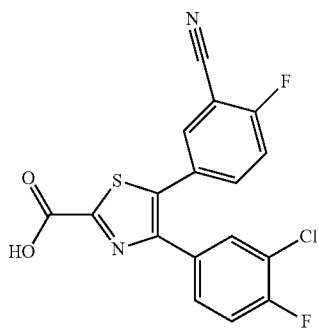 [SMILES: N#Cc1cc(-c2sc(C(=O)O)nc2-c2ccc(F)c(Cl)c2)ccc1F]

The preparation of the title compound takes place in analogy to the synthesis of the compound from Example 8A starting with the compound from Example 4A. 142 mg of the title compound having a purity of 85% (58% of theory) are obtained.

LC-MS (Method 7): $R_t$=2.27 min; MS (ESIpos): m/z=377 [M+H]$^+$.

Example 16A 4-(3-Chloro-4-fluorophenyl)-5-(3-cyanophenyl)-1,3-thiazole-2-carboxylic acid

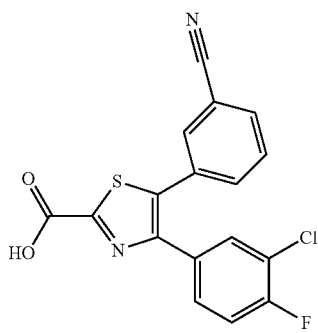 [SMILES: N#Cc1cccc(-c2sc(C(=O)O)nc2-c2ccc(F)c(Cl)c2)c1]

The preparation of the title compound takes place in analogy to the synthesis of the compound from Example 8A starting with the compound from Example 4A. 161 mg (76% of theory) of the title compound are obtained.

LC-MS (Method 7): $R_t$=2.18 min; MS (ESIpos): m/z=359 [M+H]$^+$.

$^1$H-NMR (400 MHz, DMSO-d$_6$): δ=14.4 (s, 1H), 8.00 (t, 1H), 7.95 (dt, 1H), 7.73 (dt, 1H), 7.68-7.62 (m, 2H), 7.43 (t, 1H), 7.34 (ddd, 1H).

Example 17A

N$^2$-Benzylglycinamide

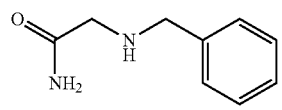 [SMILES: NC(=O)CNCc1ccccc1]

Under argon, 44.2 g (0.40 mol) of glycinamide hydrochloride are provided in 2.2 l of dichloromethane at room temperature, 112 ml (0.80 mol) of triethylamine are added and the mixture is stirred at room temperature overnight. 42.5 g (0.40 mol) of benzaldehyde are then added, and the mixture is heated under reflux on a water separator overnight. The mixture is concentrated, the residue is dissolved in 400 ml of tetrahydrofuran/methanol (1:1), 16.7 g (0.44 mol) of sodium borohydride are added a little at a time at 0° C. and the mixture is stirred at room temperature for two days. The suspension is filtered with suction and the filtrate is concentrated and dried under high vacuum. The residue is triturated with ethyl acetate, the precipitate is filtered off, the filtrate is concentrated and the residue is stirred in toluene overnight. After filtration of the solid and subsequent drying under high vacuum. 56.5 g (84% of theory) of the title compound are obtained.

$^1$H-NMR (400 MHz, DMSO-d$_6$): δ=7.36-7.28 (m, 4H), 7.27-7.19 (m, 1H), 3.68-3.64 (m, 2H), 3.03-3.00 (m, 2H).

LC-MS (Method 10): $R_t$=0.40 min; MS (ESIpos): m/z=165 [M+H]$^+$.

Example 18A

1-Benzyl-3-(hydroxymethyl)imidazolidin-4-one

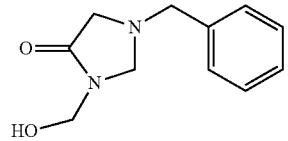 [SMILES: O=C1CN(Cc2ccccc2)CN1CO]

172 ml (6.20 mol) of a 37% formaldehyde solution are added to 56.5 g (0.34 mol) of the compound from Example 17A, and the mixture is heated under reflux for 30 minutes. The reaction mixture is extracted with dichloromethane and the combined organic phases are dried over sodium sulfate, filtered and concentrated. 74.5 g (100% of theory) of the title compound are obtained.

LC-MS (Method 5): $R_t$=0.51 min; MS (ESIpos): m/z=207 [M+H]$^+$.

Example 19A

1-Benzylimidazolidin-4-one trifluoroacetate

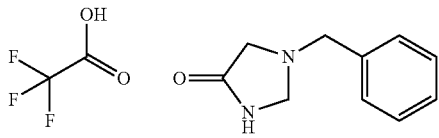

74.5 g (0.36 mol) of the compound from Example 18A are heated at 150° C. under high vacuum with destillative removal of volatile reaction products for 6 h. Purification of the residue is carried out by HPLC (column: Sunfire C18 5μ, 250×20 mm; eluent: 0.2% trifluoroacetic acid/water-acetonitrile gradient). 28.4 g (27% of theory) of the title compound are obtained.

$^1$H-NMR (400 MHz, DMSO-d$_6$): δ=8.75 (s, 1H), 7.48-7.39 (m, 5H), 4.41 (s, 2H), 4.22 (s, 2H), 3.54 (s, 2H).

LC-MS (Method 10): R$_t$=0.94 min; MS (ESIpos): m/z=177 [M—CF$_3$COOH+H]$^+$.

Example 20A

Imidazolidin-4-one trifluoroacetate

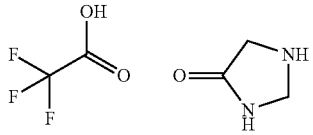

Under argon, 28.4 g (97.9 mmol) of the compound from Example 19A are dissolved in 750 ml of ethanol, and 4.5 g (42.3 mmol) of palladium on activated carbon (5%) are added. The mixture is stirred at room temperature under an atmosphere of hydrogen for 24 h. The suspension is filtered through Celite, concentrated and dried under high vacuum. 19.2 g (98% of theory) of the title compound are obtained.

$^1$H-NMR (400 MHz, DMSO-d$_6$): δ=10.1 (s, 2H), 8.89 (s, 1H), 4.55 (s, 2H), 3.63 (s, 2H).

GC-MS (Method 11): R$_t$=3.92 min; MS (EIpos): m/z=86 [M—CF$_3$COOH]$^+$.

Example 21A

3-Fluoro-5-(4,4,5,5-tetramethyl-1,3,2-dioxaborolan-2-yl)benzenecarbonitrile

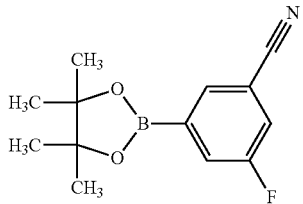 [SMILES: CC1(C)OB(c2cc(F)cc(C#N)c2)OC1(C)C]

Under argon, 3.60 g (18.0 mmol) of 3-bromo-5-fluorobenzenecarbonitrile, 5.03 g (19.8 mmol) of 4,4,4',4',5,5,5',5'-octamethyl-2,2'-bi-1,3,2-dioxaborolane and 5.30 g (54.0 mmol) of potassium acetate are provided in 72 ml of degassed 1,4-dioxane/DMSO (10/1), and 441 mg (0.54 mmol) of 1,1'-bis(diphenylphosphine)ferrocenedichloropalladium(II)/dichloromethane complex are added. The mixture is stirred at 90° C. overnight. Water is subsequently added, the phases are separated, the aqueous phase is extracted with ethyl acetate and the combined organic phases are concentrated. The crude product is purified by flash chromatography (mobile phase: cyclohexane/ethyl acetate 10:1). 4.48 g (92% of theory) of the title compound are obtained.

$^1$H-NMR (400 MHz, DMSO-d$_6$): δ=8.01 (ddd, 1H), 7.82 (s, 1H), 7.70 (ddd, 1H), 1.32 (s, 12H).

GC-MS (Method 11): R$_t$=4.94 min; MS (EIpos): m/z=247 [M]$^+$.

Example 22A (3-Cyano-5-fluorophenyl)boronic acid

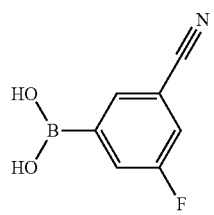 [SMILES: N#Cc1cc(F)cc(B(O)O)c1]

1.00 g (4.05 mmol) of the compound from Example 21A is provided in 40 ml of acetone, 2.60 g (12.1 mmol) of sodium periodate, 0.70 g (9.11 mmol) of ammonium acetate and 40 ml of water are added and the mixture is stirred at room temperature overnight. The mixture is subsequently concentrated, a 2N aqueous sodium hydroxide solution is added to the residue and the precipitate that remains is filtered off with suction. Using a concentrated aqueous hydrogen chloride solution, the solution is adjusted to pH 3 and cooled to 0° C. The precipitate formed is collected by suction filtration, washed with water and dried under high vacuum. 384 mg (58% of theory) of the title compound are obtained.

$^1$H-NMR (400 MHz, DMSO-d$_6$): δ=8.57 (s, 2H), 7.98 (s, 1H), 7.88 (ddd, 1H), 7.84 (dd, 1H).

LC-MS (Method 7): R$_t$=1.07 min; MS (ESIneg): m/z=164 [M–H]$^-$.

Example 23A

3-Acetyl-5-fluorobenzenecarbonitrile

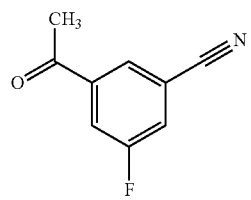

Under an argon atmosphere, 824 mg (0.900 mmol) of tris(dibenzylideneacetone)dipalladium and 1.23 g (1.98 mmol) of rac-1,1'-binaphthalene-2,2'-diylbis(diphenylphosphane) are added to 9.00 g (45.0 mmol) of 3-bromo-5-fluorobenzenecarbonitrile in toluene (300 mol). After the addition of 19.5 g (54.0 mmol) of (1-ethoxyvinyl)tributylstannane, the mixture is stirred under reflux overnight. The reaction mixture is subsequently concentrated and the residue is taken up in 300 ml of THF. After the addition of 100 ml of an aqueous 2N hydrogen chloride solution, the mixture is stirred at room temperature for 2 h. The reaction mixture is subsequently neutralized using a saturated aqueous sodium bicarbonate solution and extracted with ethyl acetate. The combined organic phases are dried over magnesium sulfate, filtered and concentrated in vacuo. The crude product is purified by flash chromatography (mobile phase: cyclohexane/ethyl acetate 9:1). 7.11 g (97% of theory) of the title compound are obtained.

¹H-NMR (400 MHz, DMSO-d₆): δ=8.28 (t, 1H), 8.18-8.14 (m, 1H), 8.08-8.04 (m, 1H), 2.65 (s, 3H).

GC-MS (Method 11): R$_t$=3.97 min; MS (EIpos): m/z=163 [M]⁺.

Example 24A

Ethyl 4-(3-cyano-5-fluorophenyl)-1,3-thiazole-2-carboxylate

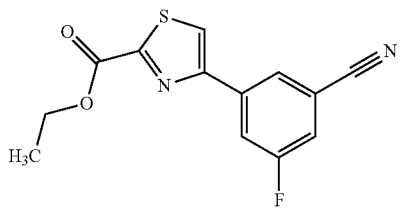 [SMILES: CCOC(=O)c1nc(-c2cc(F)cc(C#N)c2)cs1]

At room temperature, 5 drops of a conc. aqueous hydrogen chloride solution are added to 1.40 g (8.58 mmol) of the compound from Example 23A in 15 ml of conc. acetic acid. 0.44 ml (8.58 mmol) of bromine in 4 ml of conc. acetic acid are subsequently added dropwise over a period of 0.5 h. A further 0.20 ml (3.90 mmol) of bromine in 2 ml of conc. acetic acid are subsequently added dropwise, and the reaction mixture is stirred for 15 min and then poured onto ice. After extraction of the aqueous phase with ethyl acetate, the combined organic phases are dried over MgSO₄, filtered and concentrated in vacuo. 2.24 g of the solid obtained are provided in 90 ml of EtOH and heated under reflux, a solution of 1.23 g (9.25 mmol) of ethyl amino(thioxo)acetate in 10 ml of ethanol is added dropwise and the reaction mixture is stirred under reflux for 3 hours. The reaction solution is cooled and the resulting precipitate is collected by filtration. The mother liquor is concentrated in vacuo, the residue is taken up in a little ethanol and the solid formed is subsequently collected by filtration. 1.52 g (59% of theory) of the title compound are obtained after the solids are combined.

¹H-NMR (400 MHz, DMSO-d₆): δ=8.82 (s, 1H), 8.33 (s, 1H), 8.18 (d, 1H), 7.91 (d, 1H), 4.43 (q, 2H), 1.37 (t, 3H).

LC-MS (Method 1): R₁=2.35 min; MS (ESIpos): m/z=277 [M+H]⁺.

Example 25A

Ethyl 5-bromo-4-(3-cyano-5-fluorophenyl)-1,3-thiazole-2-carboxylate

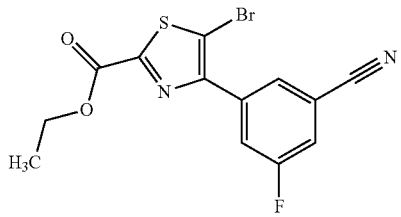 [SMILES: CCOC(=O)c1nc(-c2cc(F)cc(C#N)c2)c(Br)s1]

At room temperature, 12.8 g (79.8 mmol) of bromine and 7.83 g (79.8 mmol) of potassium acetate are added to 2.21 g (7.98 mmol) of the compound from Example 24A in 75 ml of conc. acetic acid. The mixture is stirred at 100° C. for 12 h, whereby after 6 and 9 h the same amounts of bromine (in each case 12.8 g, 79.8 mmol) and potassium acetate (in each case 7.83 g, 79.8 mmol) are again added. A 1M aqueous sodium sulfite solution is subsequently added, and the reaction solution is extracted with dichloromethane. The combined organic phases are dried over MgSO₄, filtered and concentrated under reduced pressure. The crude product is purified by flash chromatography (mobile phase: cyclohexane/ethyl acetate 20:1→10:1). 2.31 g (78% of theory) of the title compound are obtained.

¹H-NMR (400 MHz, DMSO-d₆): δ=8.15 (s, 1H), 8.05 (d, 1H), 8.03 (d, 1H), 4.42 (q, 2H), 1.35 (t, 3H).

LC-MS (Method 1): R$_t$=2.58 min; MS (ESIpos): m/z=357 [M+H]⁺.

Example 26A 5-(3-Chloro-5-fluorophenyl)-4-(3-cyano-5-fluorophenyl)-1,3-thiazole-2-carboxylic acid

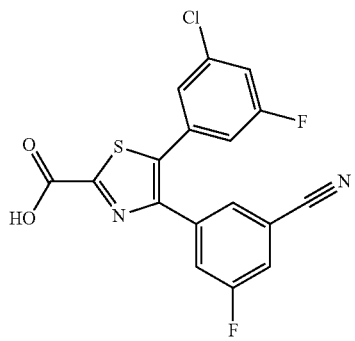 [SMILES: N#Cc1cc(F)cc(-c2nc(C(=O)O)sc2-c2cc(F)cc(Cl)c2)c1]

At room temperature, 295 mg (1.69 mmol) of the boronic acid from Example 22A are added to 400 mg (1.13 mmol) of the compound from Example 25A and 65.1 mg (0.056 mmol) of tetrakis(triphenylphosphine)palladium in 29 ml of DME. 289 mg (3.44 mmol) of sodium bicarbonate in 13 ml of water are subsequently added, and the mixture is stirred under reflux for 1 h. The reaction solution is subsequently concentrated under reduced pressure and the residue is taken up in ethyl acetate and washed with a saturated aqueous sodium chloride solution. The organic phase is dried over magnesium sulfate, filtered and concentrated. The residue is purified by preparative HPLC (RP18 column; mobile phase: acetonitrile/water gradient). 228 mg (45% of theory) of the title compound in a purity of 83% are obtained.

LC-MS (Method 5): R$_t$=1.17 min; MS (ESIpos): m/z=377 [M+H]⁺.

Example 27A

3-Acetyl-6-fluorobenzenecarbonitrile

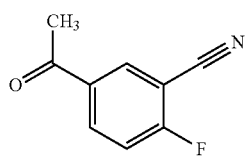

Under an argon atmosphere, 449 mg (0.490 mmol) of tris(dibenzylideneacetone)dipalladium and 671 mg (1.078 mmol) of rac-1,1'-binaphthalene-2,2'diylbis(diphenylphosphane) are added to 4.90 g (24.5 mmol) of 3-bromo-6-fluorobenzenecarbonitrile in 180 ml of toluene. After the addition of 10.6 g (29.4 mmol) of (1-ethoxyvinyl)tributylstannane, the mixture is stirred under reflux overnight. The reaction mixture is subsequently concentrated and the residue is taken up in 200 ml of THF. After the addition of an aqueous 2N hydrogen chloride solution (50 ml), the mixture is stirred at room temperature for 4 h. The reaction mixture is subsequently neutralized using a saturated aqueous sodium bicarbonate solution and extracted with ethyl acetate. The combined organic phases are dried over magnesium sulfate, filtered and concentrated under reduced pressure. The crude product is purified by flash chromatography (mobile phase: cyclohexane/ethyl acetate 10:1→3:1). 3.50 g (88% of theory) of the title compound are obtained.

$^1$H-NMR (400 MHz, DMSO-$d_6$): δ=8.55 (dd, 1H), 8.31 (ddd, 1H), 7.68 (t, 1H), 2.63 (s, 3H).

GC-MS (Method 11): $R_t$=4.34 min; MS (EIpos): m/z=163 [M]$^+$.

Example 28A

Ethyl 4-(3-cyano-4-fluorophenyl)-1,3-thiazole-2-carboxylate

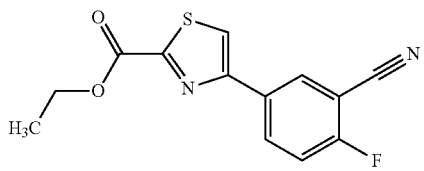 [SMILES: CCOC(=O)c1nc(-c2ccc(F)c(C#N)c2)cs1]

At room temperature, 10 drops of a conc. aqueous hydrogen chloride solution are added to 3.44 g (21.1 mmol) of the compound from Example 27A in 50 ml of conc. acetic acid. 1.08 ml (21.1 mmol) of bromine in 20 ml of conc. acetic acid are subsequently added dropwise over a period of 1 h. A further 0.20 ml (3.90 mmol) of bromine in 2 ml of conc. acetic acid are subsequently added dropwise, and the reaction mixture is stirred for 30 min and then poured onto ice. After extraction of the aqueous phase with dichloromethane, the combined organic phases are dried over MgSO$_4$, filtered and concentrated under reduced pressure. 5.40 g of the solid obtained are provided in 120 ml of EtOH, the mixture is heated under reflux, a solution of 1.93 g (14.5 mmol) of ethyl amino(thioxo)acetate in 20 ml of ethanol is added dropwise and the mixture is stirred under reflux for 5 h. The reaction solution is cooled and the resulting precipitate is collected by filtration. The mother liquor is concentrated under reduced pressure and the residue is taken up in a little ethanol, and the solid formed is subsequently collected by filtration. 3.80 g (95% of theory) of the title compound are obtained after the solids are combined.

$^1$H-NMR (400 MHz, DMSO-$d_6$): δ=8.69 (s, 1H), 8.52 (dd, 1H), 8.40 (ddd, 1H), 7.66 (t, 1H), 4.43 (q, 2H), 1.37 (t, 3H).

LC-MS (Method 5): $R_t$=1.19 min; MS (ESIpos): m/z=277 [M+H]$^+$.

Example 29A

Ethyl 5-bromo-4-(3-cyano-4-fluorophenyl)-1,3-thiazole-2-carboxylate

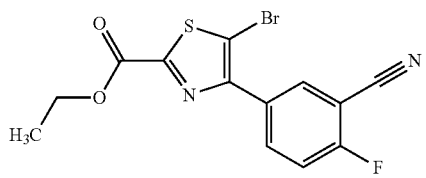 [SMILES: CCOC(=O)c1nc(-c2ccc(F)c(C#N)c2)c(Br)s1]

At room temperature, 8.10 g (50.6 mmol) of bromine and 4.97 g (50.6 mmol) of potassium acetate are added to 1.40 g (5.07 mmol) of the compound from Example 28A in 80 ml of conc. acetic acid. The mixture is stirred at 100° C. for 48 h, whereby after 24 and 36 h, bromine (in each case 4.05 g, 25.3 mmol) and potassium acetate (in each case 2.49 g, 25.3 mmol) are again added. A 1M aqueous sodium thiosulfate solution is subsequently added, and the reaction solution is extracted with dichloromethane. The combined organic phases are dried over MgSO$_4$, filtered and concentrated under reduced pressure. The crude product is purified by flash chromatography (mobile phase: cyclohexane/ethyl acetate 20:1→10:1). 1.55 g (84% of theory) of the title compound are obtained.

$^1$H-NMR (400 MHz, DMSO-$d_6$): δ=8.37 (dd, 1H), 8.30-8.20 (m, 1H), 7.73 (t, 1H), 4.42 (q, 2H), 1.35 (t, 3H).

LC-MS (Method 1): $R_t$=2.55 min; MS (ESIpos): m/z=357 [M+H]$^+$.

Example 30A 5-(3-Chloro-5-fluorophenyl)-4-(3-cyano-4-fluorophenyl)-1,3-thiazole-2-carboxylic acid

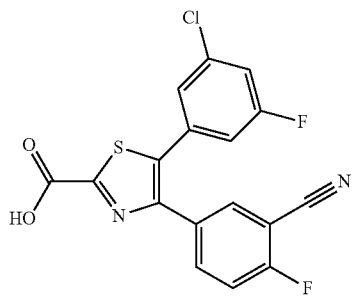 [SMILES: N#Cc1cc(-c2nc(C(=O)O)sc2-c2cc(F)cc(Cl)c2)ccc1F]

At room temperature, 256 mg (1.48 mmol) of (3-chloro-5-fluorophenyl)boronic acid are added to 350 mg (0.985 mmol) of the compound from Example 29A and 56.9 mg (0.049 mmol) of tetrakis(triphenylphosphine)palladium in 26 ml of DME. 252 mg (3.01 mmol) of sodium bicarbonate in 11 ml of water are subsequently added, and the mixture is stirred under reflux for 1 h. The reaction solution is subsequently concentrated under reduced pressure and the residue is taken up in ethyl acetate and washed with a saturated aqueous sodium chloride solution. The organic phase is dried over magnesium sulfate, filtered and concentrated. The residue is purified by preparative HPLC (RP18 column; mobile phase: acetonitrile/ water gradient). 50.0 mg (13% of theory) and 41 mg (9% of theory, purity 84%) of the title compound are obtained.

LC-MS (Method 7): $R_t$=2.15 min; MS (ESIpos): m/z=377 [M+H]$^+$.

Example 31A 5-(3-chlorophenyl)-4-(3-cyano-4-fluorophenyl)-1,3-thiazole-2-carboxylic acid

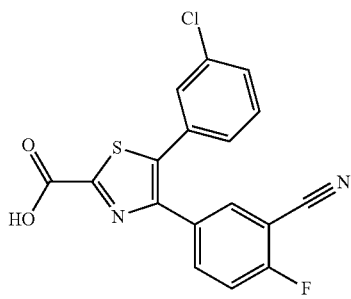 [SMILES: N#Cc1cc(-c2nc(C(=O)O)sc2-c2cccc(Cl)c2)ccc1F]

At room temperature, 231 mg (1.48 mmol) of (3-chlorophenyl)boronic acid are added to 350 mg (0.985 mmol) of the compound from Example 29A and 56.9 mg (0.049 mmol) of tetrakis(triphenylphosphine)palladium in 26 ml of DME. 252 mg (3.01 mmol) of sodium bicarbonate in 11 ml of water are subsequently added, and the mixture is stirred under reflux for 1 h. The reaction solution is subsequently concentrated under reduced pressure and the residue is taken up in ethyl acetate and washed with a saturated aqueous sodium chloride solution. The organic phase is dried over magnesium sulfate, filtered and concentrated. The residue is purified by preparative HPLC (RP18 column; mobile phase: acetonitrile/water gradient). 353 mg (100% of theory) of the title compound are obtained.

LC-MS (Method 5): $R_t$=1.17 min; MS (ESIpos): m/z=359 [M+H]$^+$.

Example 32A 4-(3-Cyano-4-fluorophenyl)-5-(3-cyano-5-fluorophenyl)-1,3-thiazole-2-carboxylic acid

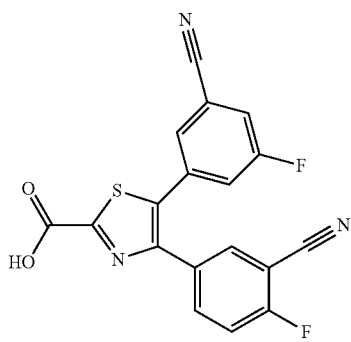 [SMILES: N#Cc1cc(F)cc(-c2sc(C(=O)O)nc2-c2ccc(F)c(C#N)c2)c1]

At room temperature, 244 mg (1.48 mmol) of the boronic acid from Example 22A are added to 350 mg (0.985 mmol) of the compound from Example 29A and 56.9 mg (0.049 mmol) of tetrakis(triphenylphosphine)palladium in 26 ml of DME. 252 mg (3.01 mmol) of sodium bicarbonate in 11 ml of water are subsequently added, and the mixture is stirred under, reflux for 1 h. The reaction solution is subsequently concentrated under reduced pressure and the residue is taken up in ethyl acetate and washed with a saturated aqueous sodium chloride solution. The organic phase is dried over magnesium sulfate, filtered and concentrated. The residue is purified by preparative HPLC (RP18 column; mobile phase: acetonitrile/water gradient). 97.6 mg (16% of theory) of the title compound having a purity of 61% are obtained.

LC-MS (Method 5): $R_t$=1.01 min; MS (ESIpos): m/z=369 [M+H]$^+$.

Example 33A 4-(3-Cyano-4-fluorophenyl)-5-(3-cyanophenyl)-1,3-thiazole-2-carboxylic acid

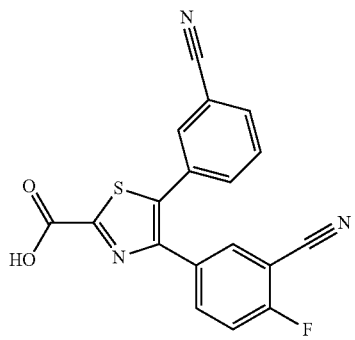 [SMILES: N#Cc1cccc(-c2sc(C(=O)O)nc2-c2ccc(F)c(C#N)c2)c1]

At room temperature, 217 mg (1.48 mmol) of (3-cyanophenyl)boronic acid are added to 350 mg (0.985 mmol) of the compound from Example 29A and 56.9 mg (0.049 mmol) of tetrakis(triphenylphosphine)palladium in 26 ml of DME. 252 mg (3.01 mmol) of sodium bicarbonate in 11 ml of water are subsequently added, and the mixture is stirred under reflux for 2 h. The reaction solution is subsequently concentrated under reduced pressure and the residue is taken up in ethyl acetate and washed with a saturated aqueous sodium chloride solution. The organic phase is dried over magnesium sulfate, filtered and concentrated. The residue is purified by preparative HPLC (RP18 column; mobile phase: acetonitrile/water gradient). 47.3 mg (14% of theory) of the title compound are obtained.

LC-MS (Method 5): $R_t$=0.97 min; MS (ESIpos): m/z=350 [M+H]$^+$.

Example 34A

Ethyl 4-(3-cyanophenyl)-1,3-thiazole-2-carboxylate

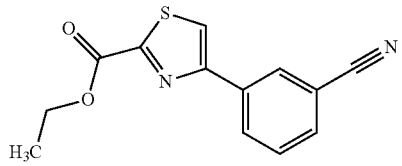 [SMILES: CCOC(=O)c1nc(-c2cccc(C#N)c2)cs1]

At room temperature, 10 drops of a conc. aqueous hydrogen chloride solution are added to 5.00 g (34.4 mmol) of 3-acetylbenzenecarbonitrile in 40 ml of conc. acetic acid. 1.8 ml (34.4 mmol) of bromine in 10 ml of conc. acetic acid are subsequently added dropwise over a period of 1 h, and after the end of the addition, the reaction mixture is poured onto ice. After extraction of the aqueous phase with dichloromethane, the combined organic phases are dried over MgSO$_4$, filtered and concentrated under reduced pressure. The solid obtained (8.00 g) is provided in 250 ml of EtOH and heated under reflux, a solution of 3.77 g (28.3 mmol) of ethyl amino(thioxo)acetate in 50 ml of ethanol is added dropwise and the mixture is stirred under reflux for 3 h. The reaction solution is cooled and the precipitate formed is collected by filtration. The mother liquor is concentrated under reduced pressure, the residue is taken up in a little ethanol and the solid formed is subsequently collected by filtration. 5.75 g (65% of theory) of the title compound are obtained after combining the solids.

$^1$H-NMR (400 MHz, DMSO-d$_6$): δ=8.74 (s, 1H), 8.45 (s, 1H), 8.35 (d, 1H), 7.88 (d, 1H), 7.77-7.62 (m, 1H), 4.43 (q, 2H), 1.37 (t, 3H).

LC-MS (Method 5): R$_t$=1.15 min; MS (ESIpos): m/z=259 [M+H]$^+$.

Example 35A

Ethyl 5-bromo-4-(3-cyanophenyl)-1,3-thiazole-2-carboxylate

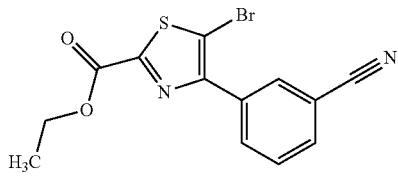 [SMILES: CCOC(=O)c1nc(-c2cccc(C#N)c2)c(Br)s1]

At room temperature, 3.18 g (19.9 mmol) of bromine and 1.95 g (19.9 mmol) of potassium acetate are added to 1.03 g (3.98 mmol) of the compound from Example 34A in 50 ml of conc. acetic acid. The mixture is stirred at 100° C. for 12 h, whereby after 6 and 9 h the same amount of bromine (in each case 3.18 g, 19.9 mmol) and potassium acetate (in each case 1.95 g, 19.9 mmol) are again added. A 1M aqueous sodium thiosulfate solution is subsequently added, and the reaction solution is extracted with dichloromethane. The combined organic phases are dried over MgSO$_4$, filtered and concentrated under reduced pressure. The crude product is purified by flash chromatography (mobile phase: cyclohexane/ethyl acetate 20:1→10:1). 1.15 g (86% of theory) of the title compound are obtained.

$^1$H-NMR (400 MHz, DMSO-d$_6$): δ=8.27 (s, 1H), 8.20 (d, 1H), 7.98 (d, 1H), 7.80-7.74 (m, 1H), 4.42 (q, 2H), 1.35 (t, 3H).

LC-MS (Method 7): R$_t$=2.14 min; MS (ESIpos): m/z=339 [M+H]$^+$.

Example 36A 5-(3-Chlorophenyl)-4-(3-cyanophenyl)-1,3-thiazole-2-carboxylic acid

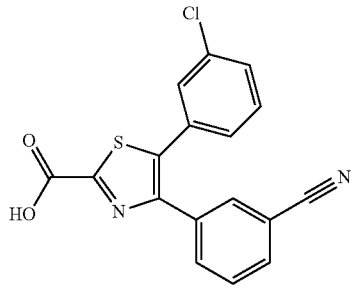 [SMILES: N#Cc1cccc(-c2nc(C(=O)O)sc2-c2cccc(Cl)c2)c1]

At room temperature, 2.2 ml of an aqueous 2M sodium carbonate solution and 30.8 mg (0.027 mmol) of tetrakis(triphenylphosphine)palladium are added to 300 mg (0.890 mmol) of the compound from Example 35A and 209 mg (1.34 mmol) of (3-chlorophenyl)boronic acid in 12 ml of DME, and the mixture is subsequently stirred at 80° C. overnight. The crude product is filtered through a short kieselguhr column and the filtrate is concentrated under reduced pressure. The residue is purified by preparative HPLC (RP18 column; mobile phase: acetonitrile/water gradient). 132 mg (37% of theory) of the title compound having a purity of 85% are obtained.

$^1$H-NMR (400 MHz, DMSO-d$_6$): δ=7.89 (s, 1H), 7.80 (d, 1H), 7.67 (d, 1H), 7.59-7.52 (m, 1H), 7.52-7.47 (m, 1H), 7.47-7.41 (m, 2H), 7.34-7.29 (m, 1H).

LC-MS (Method 1): R$_t$=2.95 min; MS (ESIpos): m/z=341 [M+H]$^+$.

Example 37A 5-(3-Chloro-5-fluorophenyl)-4-(3-cyanophenyl)-1,3-thiazole-2-carboxylic acid

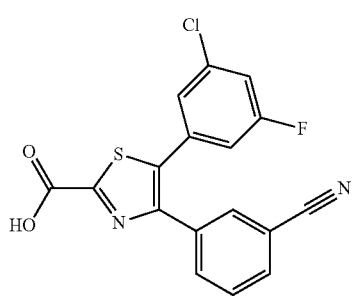 [SMILES: N#Cc1cccc(-c2nc(C(=O)O)sc2-c2cc(F)cc(Cl)c2)c1]

At room temperature, 2.2 ml of an aqueous 2M sodium carbonate solution and 30.8 mg (0.027 mmol) of tetrakis(triphenylphosphine)palladium are added to 300 mg (0.890 mmol) of the compound from Example 35A and 233 mg (1.34 mmol) of (3-chloro-5-fluorophenyl)boronic acid in 12 ml of DME, and the mixture is subsequently stirred at 80° C. overnight. The crude product is filtered through a short kieselguhr column and the filtrate is concentrated under reduced pressure. The residue is purified by preparative HPLC (RP18 column; mobile phase: acetonitrile/water gradient). 116 mg (36% of theory) of the title compound are obtained.

$^1$H-NMR (400 MHz, DMSO-d$_6$): δ=7.94 (s, 1H), 7.80 (d, 1H), 7.64 (d, 1H), 7.57-7.52 (m, 1H), 7.50 (dt, 1H), 7.28-7.25 (m, 1H), 7.22 (dt, 1H).

LC-MS (Method 1): R$_t$=3.05 min; MS (ESIpos): m/z=359 [M+H]$^+$.

Example 38A 4,5-Bis(3-cyanophenyl)-1,3-thiazole-2-carboxylic acid

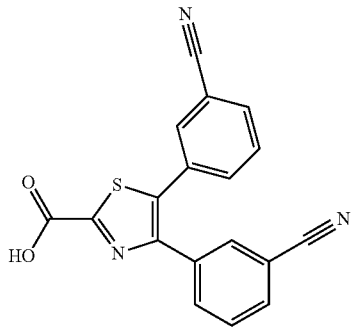 [SMILES: N#Cc1cccc(-c2nc(C(=O)O)sc2-c2cccc(C#N)c2)c1]

At room temperature, 3.0 ml of an aqueous 2M sodium carbonate solution and 41.1 mg (0.036 mmol) of tetrakis (triphenylphosphine)palladium are added to 400 mg (1.19 mmol) of the compound from Example 35A and 261 mg (1.78 mmol) of (3-cyanophenyl)boronic acid in 15 ml of DME, and the mixture is subsequently stirred at 80° C. overnight. The crude product is filtered through a short kieselguhr column and the filtrate is concentrated under reduced pressure. The residue is purified by flash chromatography (mobile phase: dichloromethane). 104 mg (26% of theory) of the title compound are obtained.

$^1$H-NMR (400 MHz, DMSO-d$_6$): δ=7.90-7.77 (m, 4H), 7.67-7.50 (m, 4H).

LC-MS (Method 5): R$_t$=0.91 min; MS (ESIpos): m/z=332 [M+H]$^+$.

Example 39A 4,5-Bis(3-chlorophenyl)-1,3-thiazole-2-carboxylic acid

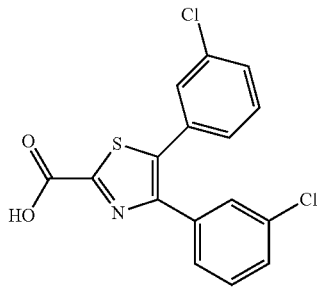 [SMILES: O=C(O)c1nc(-c2cccc(Cl)c2)c(-c2cccc(Cl)c2)s1]

At room temperature, 7.2 ml of an aqueous 2M sodium carbonate solution and 167 mg (0.144 mmol) of tetrakis (triphenylphosphine)palladium are added to 1.00 g (2.88 mmol) of the compound from Example 5A and 677 mg (4.33 mmol) of (3-chlorophenyl)boronic acid in 40 ml of DME, and the mixture is subsequently stirred at 80° C. overnight. A saturated aqueous ammonium chloride solution is added, and the reaction mixture is subsequently extracted with dichloromethane. The organic phase is dried over magnesium sulfate, filtered and concentrated under reduced pressure. The residue is purified by preparative HPLC (RP18 column; mobile phase: acetonitrile/water gradient). 173 mg (17% of theory) of the title compound are obtained.

$^1$H-NMR (400 MHz, DMSO-d$_6$): δ=7.51 (s, 1H), 7.49-7.30 (m, 5H), 7.30-7.22 (m, 2H).

LC-MS (Method 5): R$_t$=1.29 min; MS (ESIpos): m/z=350 [M+H]$^+$.

Example 40A 4-(3-Chlorophenyl)-5-(3-cyano-5-fluorophenyl)-1,3-thiazole-2-carboxylic acid

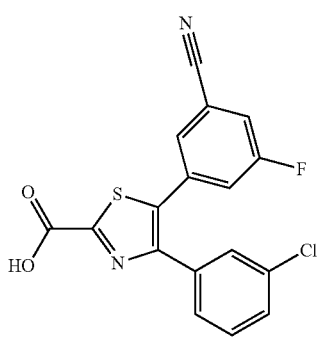 [SMILES: N#Cc1cc(F)cc(-c2sc(C(=O)O)nc2-c2cccc(Cl)c2)c1]

At room temperature, 7.2 ml of an aqueous 2M sodium carbonate solution and 167 mg (0.144 mmol) of tetrakis (triphenylphosphine)palladium are added to 1.00 g (2.89 mmol) of the compound from Example 5A and 714 mg (4.33 mmol) of the boronic acid from Example 22A in 40 ml of DME, and the mixture is subsequently stirred at 80° C. for 24 h. A saturated aqueous ammonium chloride solution is added, and the reaction mixture is subsequently extracted with dichloromethane. The organic phase is dried over magnesium sulfate, filtered and concentrated under reduced pressure. The residue is purified by preparative HPLC (RP18 column; mobile phase: acetonitrile/water gradient). 606 mg (53% of theory) of the title compound having a purity of 90% are obtained.

LC-MS (Method 5): R$_t$=1.10 min; MS (ESIpos): m/z=359 [M+H]$^+$.

Exemplary Embodiments

Example 1

1-{[4-(3-Chloro-4-fluorophenyl)-5-(3-chloro-5-fluorophenyl)-1,3-thiazole-2-yl]carbonyl}imidazolidin-4-one

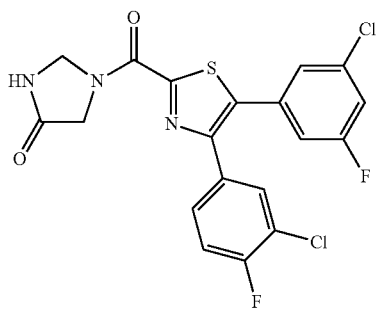 [SMILES: O=C1CN(C(=O)c2nc(-c3ccc(F)c(Cl)c3)c(-c3cc(F)cc(Cl)c3)s2)CN1]

93.0 mg (0.24 mmol) of the compound from Example 8A, 53.0 mg (0.27 mmol) of the compound from Example 20A and 188 mg (0.36 mmol) of PyBOP are provided in 3 ml of tetrahydrofuran, and 88 µl (0.51 mmol) of N,N-diisopropylethylamine are added at room temperature. The reaction mixture is stirred at room temperature overnight and subsequently purified by preparative HPLC (RP18 column; mobile phase: acetonitrile/water gradient). 66.0 mg (60% of theory) of the title compound are obtained.

$^1$H-NMR (400 MHz, DMSO-d$_6$): δ=8.81 (s, 0.6H), 8.72 (s, 0.4H), 7.76-7.71 (m, 1H), 7.60 (dt, 1H), 7.50-7.33 (m, 4H), 5.49 (s, 0.8H), 4.94 (s, 1.2H), 4.59 (s, 1.2H), 4.03 (s, 0.8H).

LC-MS (Method 1): R$_t$=2.65 min; MS (ESIpos): m/z=454 [M+H]$^+$.

Example 2

1-{[4-(3-Chloro-4-fluorophenyl)-5-(3-chlorophenyl)-1,3-thiazole-2-yl]carbonyl}imidazolidin-4-one

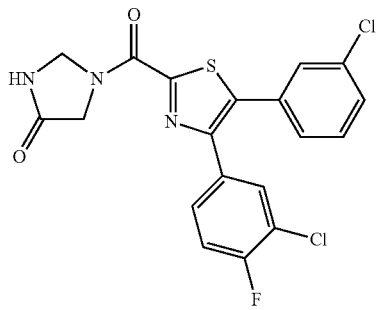 [SMILES: O=C1CN(C(=O)c2nc(-c3ccc(F)c(Cl)c3)c(-c3cccc(Cl)c3)s2)CN1]

80.0 mg (0.22 mmol) of the compound from Example 9A, 47.8 mg (0.24 mmol) of the compound from Example 20A and 170 mg (0.33 mmol) of PyBOP are provided in 3.2 ml of tetrahydrofuran, and 79 µl (0.46 mmol) of N,N-diisopropylethylamine are added at room temperature. The mixture is stirred at room temperature overnight. The reaction mixture is subsequently taken up in water and concentrated and the precipitate is collected by suction filtration resulting in 40.0 mg (42% of theory) of the title compound.

$^1$H-NMR (400 MHz, DMSO-d$_6$): δ=8.80 (s, 0.6H), 8.71 (s, 0.4H), 7.70 (d, 1H), 7.58-7.54 (m, 2H), 7.52-7.36 (m, 4H), 5.50 (s, 0.8H), 4.94 (s, 1.2H), 4.60 (s, 1.2H), 4.03 (s, 0.8H).

LC-MS (Method 1): R$_t$=2.63 min; MS (ESIpos): m/z=436 [M+H]$^+$.

Example 3

1-{[5-(3-Chloro-5-fluorophenyl)-4-(3-chlorophenyl)-1,3-thiazole-2-yl]carbonyl}imidazolidin-4-one

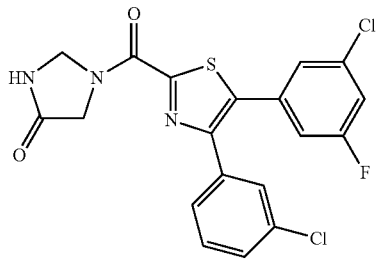 [SMILES: O=C1CN(C(=O)c2nc(-c3cccc(Cl)c3)c(-c3cc(F)cc(Cl)c3)s2)CN1]

The preparation of the title compound takes place in analogy to the synthesis of the compound from Example 1 starting with the compound from Example 10A. 40.0 mg (41% of theory) of the title compound are obtained.

$^1$H-NMR (400 MHz, DMSO-d$_6$): δ=8.81 (s, 0.6H), 8.71 (s, 0.4H), 7.63-7.56 (m, 2H), 7.50-7.45 (m, 1H), 7.45-7.32 (m, 4H), 5.49 (s, 0.8H), 4.94 (s, 1.2H), 4.59 (s, 1.2H), 4.03 (s, 0.8H).

LC-MS (Method 7): R$_t$=2.19 min; MS (ESIpos): m/z=436 [M+H]$^+$.

Example 4

1-{[5-(3-Chloro-4-fluorophenyl)-4-(3-chlorophenyl)-1,3-thiazole-2-yl]carbonyl}imidazolidin-4-one

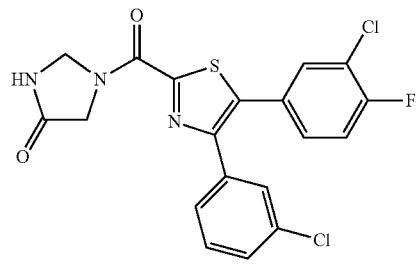 [SMILES: O=C1CN(C(=O)c2nc(-c3cccc(Cl)c3)c(-c3ccc(F)c(Cl)c3)s2)CN1]

59.0 mg (0.16 mmol) of the compound from Example 11A, 35.3 mg (0.18 mmol) of the compound from Example 20A and 125 mg (0.24 mmol) of PyBOP are provided in 3 ml of tetrahydrofuran, and 0.06 ml (0.34 mmol) of N,N-diisopropylethylamine are added at room temperature. The mixture is stirred at room temperature overnight. The reaction mixture is subsequently taken up in water and concentrated and the precipitate is collected by suction filtration and recrystallized from ethyl acetate, resulting in 20.0 mg (29% of theory) of the title compound.

$^1$H-NMR (400 MHz, DMSO-d$_6$): δ=8.81 (s, 0.6H), 8.71 (s, 0.4H), 7.73 (dt, 1H), 7.59-7.49 (m, 2H), 7.48-7.33 (m, 4H), 5.50 (s, 0.8H), 4.94 (s, 1.2H), 4.59 (s, 1.2H), 4.03 (s, 0.8H).

LC-MS (Method 1): R$_t$=2.60 min; MS (ESIpos): m/z=436 [M+H]$^+$.

Example 5

5-{4-(3-Chlorophenyl)-2-[(4-oxoimidazolidin-1-yl)carbonyl]-1,3-thiazole-5-yl}-2-fluorobenzenecarbonitrile

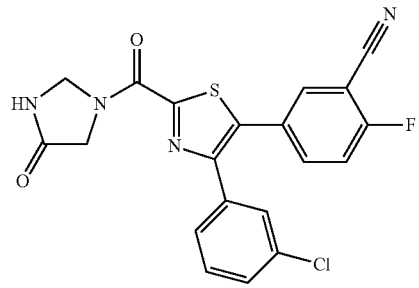 [SMILES: N#Cc1cc(-c2sc(C(=O)N3CNC(=O)C3)nc2-c2cccc(Cl)c2)ccc1F]

42.4 mg (0.12 mmol) of the compound from Example 12A, 26.0 mg (0.13 mmol) of the compound from Example 20A and 92.3 mg (0.18 mmol) of PyBOP are provided in 2 ml of tetrahydrofuran, and 66 µl (0.38 mmol) of N,N-diisopropylethylamine are added at room temperature. The reaction mixture is stirred at room temperature overnight and subsequently purified by preparative HPLC (RP18 column; mobile phase: acetonitrile/water gradient with the addition of 0.1% formic acid). 33.7 mg (65% of theory) of the title compound are obtained.

¹H-NMR (400 MHz, DMSO-d₆): δ=8.81 (s, 0.6H), 8.71 (s, 0.4H), 8.14 (dt, 1H), 7.79 (ddd, 1H), 7.66-7.57 (m, 2H), 7.49-7.29 (m, 3H), 5.50 (s, 0.8H), 4.94 (s, 1.2H), 4.60 (s, 1.2H), 4.03 (s, 0.8H).

LC-MS (Method 7): R$_t$=1.88 min; MS (ESIpos): m/z=427 [M+H]⁺.

Example 6

1-{[4-(3-Chloro-5-fluorophenyl)-5-(3-chlorophenyl)-1,3-thiazol-2-yl]carbonyl}imidazolidin-4-one

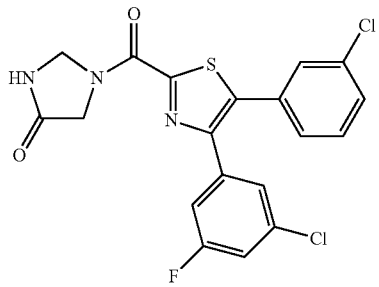 [SMILES: O=C1CN(C(=O)c2nc(-c3cc(F)cc(Cl)c3)c(-c3cccc(Cl)c3)s2)CN1]

The preparation of the title compound takes place in analogy to the synthesis of the compound from Example 4 starting with the compound from Example 11A. 4.5 mg (19% of theory) of the title compound are obtained.

¹H-NMR (400 MHz, DMSO-d₆): δ=8.81 (s, 0.6H), 8.70 (s, 0.4H), 7.61-7.56 (m, 2H), 7.54-7.47 (m, 2H), 7.42-7.38 (m, 1H), 7.34 (dt, 1H), 7.28 (tt, 1H), 5.50 (s, 0.8H), 4.94 (s, 1.2H), 4.61 (s, 1.2H), 4.03 (s, 0.8H).

LC-MS (Method 7): R$_t$=2.15 min; MS (ESIpos): m/z=436 [M+H]⁺.

Example 7

3-{4-(3-Chlorophenyl)-2-[(4-oxoimidazolidin-1-yl)carbonyl]-1,3-thiazol-5-yl}benzenecarbonitrile

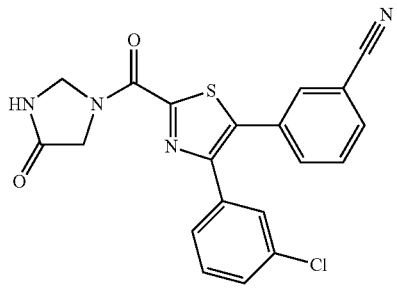 [SMILES: N#Cc1cccc(-c2sc(C(=O)N3CNC(=O)C3)nc2-c2cccc(Cl)c2)c1]

The preparation of the title compound takes place in analogy to the synthesis of the compound from Example 5 starting with the compound from Example 7A. 12.0 mg (22% of theory) of the title compound are obtained.

¹H-NMR (400 MHz, DMSO-d₆): δ=8.81 (s, 0.6H), 8.71 (s, 0.4H), 8.01-7.92 (m, 2H), 7.75-7.71 (m, 1H), 7.66 (t, 1H), 7.56-7.53 (m, 1H), 7.49-7.37 (m, 2H), 7.34 (tt, 1H), 5.50 (s, 0.8H), 4.95 (s, 1.2H), 4.60 (s, 1.2H), 4.03 (s, 0.8H).

LC-MS (Method 5): R$_t$=1.16 min; MS (ESIpos): m/z=409 [M+H]⁺.

Example 8

1-({4-(3-Chlorophenyl)-5-[3-(trifluoromethyl)phenyl]-1,3-thiazol-2-yl}carbonyl)imidazolidin-4-one

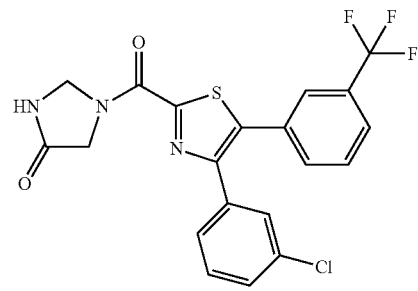 [SMILES: O=C1CN(C(=O)c2nc(-c3cccc(Cl)c3)c(-c3cccc(C(F)(F)F)c3)s2)CN1]

100 mg (0.17 mmol) of the compound from Example 14A, 15.8 mg (0.18 mmol) of 4-imidazolidinone and 95.3 mg (0.18 mmol) of PyBOP are provided in 1.2 ml of tetrahydrofuran, and 32 (0.18 mmol) of N,N-diisopropylethylamine are added at room temperature. The reaction mixture is stirred at room temperature overnight and subsequently purified by preparative HPLC (RP18 column; mobile phase: acetonitrile/water gradient) and additionally by preparative thin-layer chromatography (silica gel; mobile phase dichloromethane/methanol 10/1). 34.8 mg (42% of theory) of the title compound are obtained.

¹H-NMR (400 MHz, DMSO-d₆): δ=8.81 (s, 0.6H), 8.71 (s, 0.4H), 7.85 (d, 1H), 7.78-7.68 (m, 3H), 7.54-7.51 (m, 1H), 7.49-7.34 (m, 3H), 5.50 (s, 0.8H), 4.95 (s, 1.2H), 4.60 (s, 1.2H), 4.04 (s, 0.8H).

LC-MS (Method 5): R$_t$=1.34 min; MS (ESIpos): m/z=452 [M+H]⁺.

Example 9

5-{4-(3-Chloro-4-fluorophenyl)-2-[(4-oxoimidazolidin-1-yl)carbonyl]-1,3-thiazol-5-yl}-2-fluorobenzenecarbonitrile

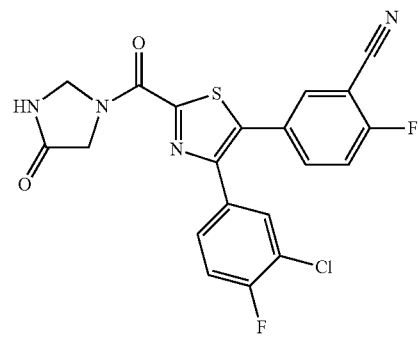 [SMILES: N#Cc1cc(-c2sc(C(=O)N3CNC(=O)C3)nc2-c2ccc(F)c(Cl)c2)ccc1F]

The preparation of the title compound takes place in analogy to the synthesis of the compound from Example 5 starting with the compound from Example 15A. 17.3 mg (35% of theory) of the title compound are obtained.

¹H-NMR (400 MHz, DMSO-d₆): δ=8.81 (s, 0.6H), 8.72 (s, 0.4H), 8.16 (dt, 1H), 7.82-7.73 (m, 2H), 7.62 (t, 1H), 7.46-7.33 (m, 2H), 5.50 (s, 0.8H), 4.94 (s, 1.2H), 4.60 (s, 1.2H), 4.03 (s, 0.8H).

LC-MS (Method 7): $R_t$=1.91 min; MS (ESIpos): m/z=445 [M+H]$^+$.

Example 10

3-{(4-(3-Chloro-4-fluorophenyl)-2-[(4-oxoimidazolidin-1-yl)carbonyl]-1,3-thiazole-5-yl}benzenecarbonitrile

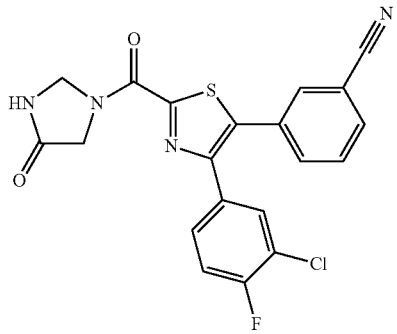 [SMILES: N#Cc1cccc(-c2sc(C(=O)N3CNC(=O)C3)nc2-c2ccc(F)c(Cl)c2)c1]

The preparation of the title compound takes place in analogy to the synthesis of the compound from Example 5 starting with the compound from Example 16A. 9.3 mg (15% of theory) of the title compound are obtained.

$^1$H-NMR (400 MHz, DMSO-d$_6$): δ=8.81 (s, 0.6H), 8.72 (s, 0.4H), 8.03-8.00 (m, 1H), 7.95 (d, 1H), 7.75-7.63 (m, 3H), 7.48-7.34 (m, 2H), 5.50 (s, 0.8H), 4.94 (s, 1.2H), 4.60 (s, 1.2H), 4.04 (s, 0.8H).

LC-MS (Method 7): $R_t$=1.85 min; MS (ESIpos): m/z=427 [M+H]$^+$.

Example 11

3-{4-(3-Chloro-4-fluorophenyl)-2-[(4-oxoimidazolidin-1-yl)carbonyl]-1,3-thiazole-5-yl}fluorobenzenecarbonitrile

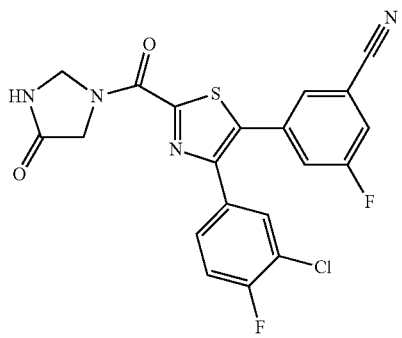 [SMILES: N#Cc1cc(F)cc(-c2sc(C(=O)N3CNC(=O)C3)nc2-c2ccc(F)c(Cl)c2)c1]

Under argon, 108 mg (0.25 mmol) of the compound from Example 7A and 61.9 mg (0.38 mmol) of the compound from Example 22A are provided in 3.5 ml of 1,2-dimethoxyethane, and 1.3 ml (1.25 mmol) of an aqueous sodium bicarbonate solution (10%) and 8.7 mg (8 mmol) of tetrakis(triphenylphosphine)palladium(0) are added. The mixture is stirred at 80° C. overnight. The mixture is concentrated and the residue is purified by preparative HPLC (RP18 column; mobile phase: acetonitrile/water gradient) and additionally by preparative thin-layer chromatography (silica gel; mobile phase ethyl acetate/cyclohexane 1/1), resulting in 4.3 mg (4% of theory) of the title compound.

$^1$H-NMR (400 MHz, DMSO-d$_6$): δ=8.81 (s, 0.6H), 8.72 (s, 0.4H), 8.01 (d, 1H), 7.88-7.85 (m, 1H), 7.77-7.71 (m, 2H), 7.48-7.33 (m, 2H), 5.50 (s, 0.8H), 4.94 (s, 1.2H), 4.60 (s, 1.2H), 4.04 (s, 0.8H).

LC-MS (Method 7): $R_t$=1.91 min; MS (ESIpos): m/z=445 [M+H]$^+$.

Example 12

3-{5-(3-Chloro-5-fluorophenyl)-2-[(4-oxoimidazolidin-1-yl)carbonyl]-1,3-thiazole-4-yl}fluorobenzenecarbonitrile

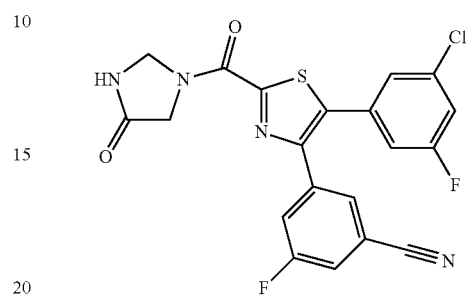

65.0 mg (0.143 mmol) of the compound from Example 26A having a purity of 83%, 31.5 mg (0.158 mmol) of the compound from Example 20A and 112 mg (0.215 mmol) of PyBOP are provided in 6.0 ml of tetrahydrofuran, and 80 μl (0.458 mmol) of N,N-diisopropylethylamine are added at room temperature. The mixture is stirred at room temperature overnight and the reaction solution is diluted with dichloromethane and subsequently washed with water. The organic phase is dried over magnesium sulfate, filtered and concentrated under reduced pressure, and the crude product is then taken up in a little acetonitrile and the solid formed is subsequently collected by filtration. 30.0 mg (47% of theory) of the title compound are obtained.

$^1$H-NMR (400 MHz, DMSO-d$_6$): δ=8.81 (s, 0.6H), 8.71 (s, 0.4H), 7.93 (d, 1H), 7.82 (d, 1H), 7.74-7.57 (m, 2H), 7.50-7.31 (m, 2H), 5.51 (s, 0.8H), 4.95 (s, 1.2H), 4.63 (s, 1.2H), 4.04 (s, 0.8H).

LC-MS (Method 5): $R_t$=1.25 min; MS (ESIpos): m/z=445 [M+H]$^+$.

Example 13

5-{5-(3-Chloro-5-fluorophenyl)-2-[(4-oxoimidazolidin-1-yl)carbonyl]-1,3-thiazole-4-yl}-2-fluorobenzenecarbonitrile

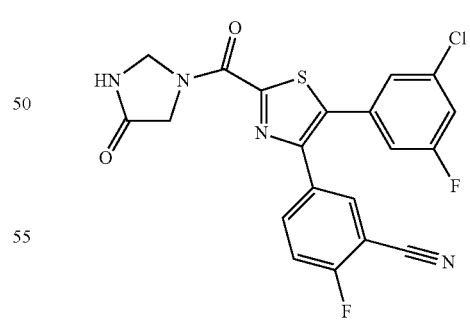

45.0 mg (0.119 mmol) of the compound from Example 30A having a purity of 84%, 26.3 mg (0.131) of the compound from Example 20A and 93.2 mg (0.179 mmol) of PyBOP are provided in 4.8 ml of tetrahydrofuran, and 67 μl (0.382 mmol) of N,N-diisopropylethylamine are added at room temperature. The reaction solution is stirred at room temperature overnight, diluted with dichloromethane and subsequently washed with a 1N aqueous hydrogen chloride solution. The organic phase is dried over magnesium sulfate, filtered and concentrated under reduced pressure, and the crude product is then purified by preparative HPLC (RP18 column; mobile phase: acetonitrile/water gradient). 25.0 mg (56% of theory) of the title compound are obtained.

$^1$H-NMR (400 MHz, DMSO-d$_6$): δ=8.80 (s, 0.6H), 8.73 (s, 0.4H), 8.20-8.09 (m, 1H), 7.77 (m, 1H), 7.67-7.50 (m, 2H), 7.41 (s, 1H), 7.36 (d, 1H), 5.50 (s, 0.8H), 4.94 (s, 1.2H), 4.62 (s, 1.2H), 4.04 (s, 0.8H).

LC-MS (Method 5): R$_t$=1.26 min; MS (ESIpos): m/z=445 [M+H]$^+$.

Example 14

5-{5-(3-Chlorophenyl)-2-[(4-oxoimidazolidin-1-yl)carbonyl]-1,3-thiazole-4-yl}-2-fluorobenzenecarbonitrile

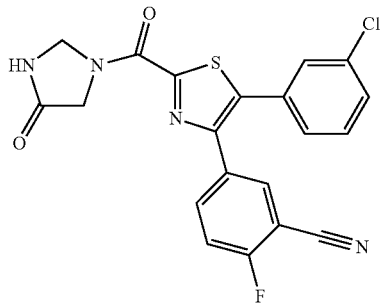 [SMILES: N#Cc1cc(-c2nc(C(=O)N3CNC(=O)C3)sc2-c2cccc(Cl)c2)ccc1F]

80.0 mg (0.223 mmol) of the compound from Example 31A, 49.1 mg (0.245 mmol) of the compound from Example 20A and 174 mg (0.334 mmol) of PyBOP are provided in 7.0 ml of tetrahydrofuran, and 124 µl (0.714 mmol) of N,N-diisopropylethylamine are added at room temperature. The reaction solution is stirred at room temperature overnight, diluted with dichloromethane and subsequently washed with a 1N aqueous hydrogen chloride solution. The organic phase is dried over magnesium sulfate, filtered and concentrated under reduced pressure, and the crude product is then purified by preparative HPLC (RP18 column; mobile phase: acetonitrile/water gradient). 42.5 mg (45% of theory) of the title compound are obtained.

$^1$H-NMR (400 MHz, DMSO-d$_6$): δ=8.80 (s, 0.6H), 8.73 (s, 0.4H), 8.17-8.05 (m, 1H), 7.85-7.68 (m, 1H), 7.60-7.52 (m, 3H), 7.48 (t, 1H), 7.37 (d, 1H), 5.51 (s, 0.8H), 4.94 (s, 1.2H), 4.62 (s, 1.2H), 4.04 (s, 0.8H).

LC-MS (Method 1): R$_t$=2.32 min; MS (ESIpos): m/z=427 [M+H]$^+$.

Example 15

5-{5-(3-Cyano-5-fluorophenyl)-2-[(4-oxoimidazolidin-1-yl)carbonyl]-1,3-thiazole-4-yl}-2-fluorobenzenecarbonitrile

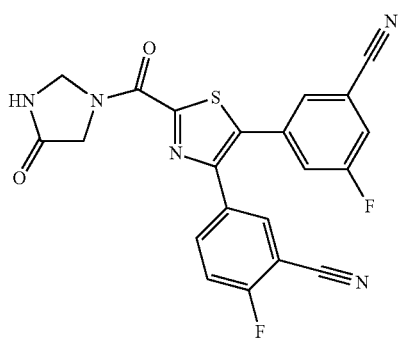 [SMILES: N#Cc1cc(F)cc(-c2sc(C(=O)N3CNC(=O)C3)nc2-c2ccc(F)c(C#N)c2)c1]

45.0 mg of the compound from Example 32A having a purity of 61% (0.075 mmol), 16.5 mg (0.082 mmol) of the compound from Example 20A and 58.3 mg (0.112 mmol) of PyBOP are provided in 3 ml of tetrahydrofuran, and 42 µl (0.239 mmol) of N,N-diisopropylethylamine are added at room temperature. The reaction solution is stirred at room temperature overnight, diluted with dichloromethane and subsequently washed with a 1N aqueous hydrogen chloride solution. The organic phase is dried over magnesium sulfate, filtered and concentrated under reduced pressure, acetonitrile is then added to the crude product and the solid formed is subsequently collected by filtration. 17.4 mg (53% of theory) of the title compound are obtained.

$^1$H-NMR (400 MHz, DMSO-d$_6$): δ=8.81 (s, 0.6H), 8.74 (s, 0.4H), 8.22-8.11 (m, 1H), 8.01 (d, 1H), 7.86 (s, 1H), 7.82-7.68 (m, 2H), 7.54 (td, 1H), 5.51 (s, 0.8H), 4.95 (s, 1.2H), 4.62 (s, 1.2H), 4.04 (s, 0.8H).

LC-MS (Method 5): R$_t$=1.11 min; MS (ESIpos): m/z=436 [M+H]$^+$.

Example 16

5-{5-(3-Cyanophenyl)-2-[(4-oxoimidazolidin-1-yl)carbonyl]-1,3-thiazole-4-yl}-2-fluorobenzenecarbonitrile

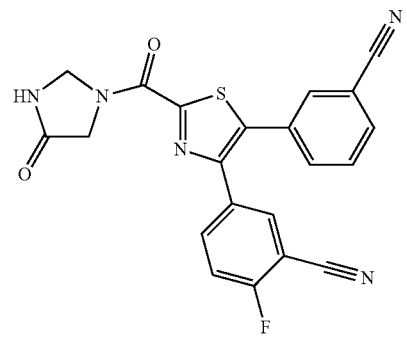 [SMILES: N#Cc1cccc(-c2sc(C(=O)N3CNC(=O)C3)nc2-c2ccc(F)c(C#N)c2)c1]

45.0 mg (0.129 mmol) of the compound from Example 33A, 28.4 mg (0.142 mmol) of the compound from Example 20A and 101 mg (0.193 mmol) of PyBOP are provided in 4.0 ml of tetrahydrofuran, and 72 µl (0.412 mmol) of N,N-diisopropylethylamine are added at room temperature. The reaction solution is stirred at room temperature overnight, diluted with dichloromethane and subsequently washed with a 1N aqueous hydrogen chloride solution. The organic phase is dried over magnesium sulfate, filtered and concentrated under reduced pressure, the crude product is then taken up in a little acetonitrile and the solid formed is subsequently collected by filtration. The crude product is purified by preparative HPLC (RP18 column; mobile phase: acetonitrile/water gradient). 15.2 mg (28% of theory) of the title compound are obtained.

$^1$H-NMR (400 MHz, DMSO-d$_6$): δ=8.81 (s, 0.6H), 8.73 (s, 0.4H), 8.14-8.09 (m, 1H), 8.02 (d, 1H), 7.96 (d, 1H), 7.80-7.69 (m, 2H), 7.68-7.62 (m, 1H), 7.58-7.50 (m, 1H), 5.51 (s, 0.8H), 4.95 (s, 1.2H), 4.62 (s, 1.2H), 4.04 (s, 0.8H).

LC-MS (Method 7): R$_t$=1.68 min; MS (ESIpos): m/z=418 [M+H]$^+$.

Example 17

3-{(5-(3-Chlorophenyl)-2-[(4-oxoimidazolidin-1-yl)carbonyl]-1,3-thiazole-4-yl}benzenecarbonitrile

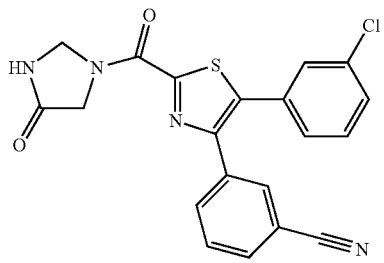 [SMILES: N#Cc1cccc(-c2nc(C(=O)N3CNC(=O)C3)sc2-c2cccc(Cl)c2)c1]

80.0 mg of the compound from Example 36A having a purity of 85% (0.235 mmol), 51.7 mg (0.258 mmol) of the compound from Example 20A and 183 mg (0.352 mmol) of PyBOP are provided in 4.5 ml of tetrahydrofuran, and 131 μl (0.751 mmol) of N,N-diisopropylethylamine are added at room temperature. The reaction solution is stirred at room temperature overnight, diluted with dichloromethane and subsequently washed with water. The organic phase is dried over magnesium sulfate, filtered and concentrated under reduced pressure, and the crude product is then pre-purified by flash chromatography (mobile phase: dichloromethane/methanol 100:1). The crude product is subsequently purified by preparative HPLC (RP18 column; mobile phase: acetonitrile/water gradient), and the resulting solid is taken up in diethyl ether/acetonitrile, stirred for 30 min and then filtered. 60.0 mg (74% of theory) of the title compound are obtained.

$^1$H-NMR (400 MHz, DMSO-$d_6$): δ=8.81 (s, 0.6H), 8.72 (s, 0.4H), 7.98 (s, 1H), 7.86 (d, 1H), 7.79-7.67 (m, 1H), 7.64-7.52 (m, 3H), 7.49 (t, 1H), 7.37 (d, 1H), 5.51 (s, 0.8H), 4.95 (s, 1.2H), 4.62 (s, 1.2H), 4.04 (s, 0.8H).

LC-MS (Method 7): $R_t$=1.90 min; MS (ESIpos): m/z=409 [M+H]$^+$.

Example 18

3-{5-(3-Chloro-5-fluorophenyl)-2-[(4-oxoimidazolidin-1-yl)carbonyl]-1,3-thiazole-4-yl}benzenecarbonitrile

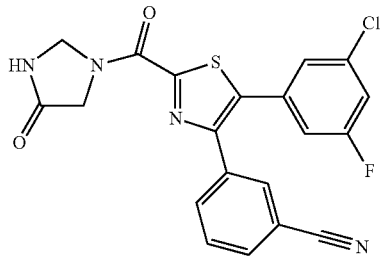 [SMILES: N#Cc1cccc(-c2nc(C(=O)N3CNC(=O)C3)sc2-c2cc(F)cc(Cl)c2)c1]

80.0 mg (0.223 mmol) of the compound from Example 37A, 49.1 mg (0.245 mmol) of the compound from Example 20A and 174 mg (0.334 mmol) of PyBOP are provided in 4.5 ml of tetrahydrofuran, and 124 μl (0.714 mmol) of N,N-diisopropylethylamine are added at room temperature. The reaction solution is stirred at room temperature overnight, diluted with dichloromethane and subsequently washed with water. The organic phase is dried over magnesium sulfate, filtered and concentrated under reduced pressure, and the crude product is then pre-purified by flash chromatography (mobile phase: dichloromethane/methanol 100:1). The crude product is subsequently purified by preparative HPLC (RP18 column; mobile phase: acetonitrile/water gradient), and the resulting solid is taken up in diethyl ether/acetonitrile, stirred for 30 min and subsequently filtered. 58.0 mg (61% of theory) of the title compound are obtained.

$^1$H-NMR (DMSO-$d_6$): δ=8.81 (s, 0.6H), 8.72 (s, 0.4H), 8.02 (d, 1H), 7.92-7.83 (m, 1H), 7.79-7.67 (m, 1H), 7.65-7.57 (m, 2H), 7.39 (d, 1H), 7.35 (dd, 1H), 5.51 (s, 0.8H), 4.94 (s, 1.2H), 4.62 (s, 1.2H), 4.04 (s, 0.8H).

LC-MS (Method 7): $R_t$=1.93 min; MS (ESIpos): m/z=427 [M+H]$^+$.

Example 19

3,3'-{2-[(4-Oxoimidazolidin-1-yl)carbonyl]-1,3-thiazole-4,5-diyl}benzenecarbonitrile

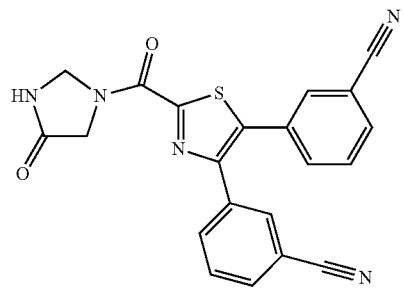 [SMILES: N#Cc1cccc(-c2nc(C(=O)N3CNC(=O)C3)sc2-c2cccc(C#N)c2)c1]

55.0 mg (0.166 mmol) of the compound from Example 38A, 36.5 mg (0.183 mmol) of the compound from Example 20A and 130 mg (0.249 mmol) of PyBOP are provided in 5.5 ml of tetrahydrofuran, and 93 μl (0.531 mmol) of N,N-diisopropylethylamine are added at room temperature. The reaction solution is stirred at room temperature overnight, diluted with dichloromethane and subsequently washed with water. The organic phase is dried over magnesium sulfate, filtered and concentrated under reduced pressure, and the crude product is then pre-purified by flash chromatography (mobile phase: dichloromethane/methanol 100:1). The crude product is subsequently purified by preparative HPLC (RP18 column; mobile phase: acetonitrile/water gradient). 37.0 mg (56% of theory) of the title compound are obtained.

$^1$H-NMR (400 MHz, DMSO-$d_6$): δ=8.81 (s, 0.6H), 8.72 (s, 0.4H), 8.02-7.98 (m, 2H), 7.96 (d, 1H), 7.87 (d, 1H), 7.76-7.53 (m, 4H), 5.52 (s, 0.8H), 4.95 (s, 1.2H), 4.62 (s, 1.2H), 4.04 (s, 0.8H).

LC-MS (Method 5): $R_t$=1.04 min; MS (ESIpos): m/z=400 [M+H]$^+$.

Example 20

1-{[4,5-Bis(3-chlorophenyl)-1,3-thiazole-2-yl]carbonyl}imidazolidin-4-one

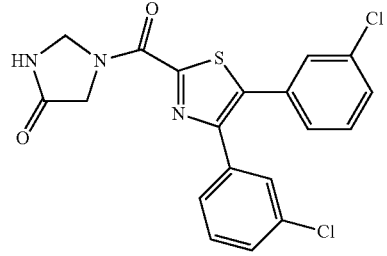 [SMILES: O=C1CN(C(=O)c2nc(-c3cccc(Cl)c3)c(-c3cccc(Cl)c3)s2)CN1]

100 mg (0.286 mmol) of the compound from Example 39A, 62.9 mg (0.314 mmol) of the compound from Example 20A and 223 mg (0.428 mmol) of PyBOP are provided in 4.0 ml of tetrahydrofuran, and 159 μl (0.914 mmol) of N,N- diisopropylethylamine are added at room temperature. The reaction solution is stirred at room temperature overnight, diluted with dichloromethane and subsequently washed with a 1N aqueous hydrogen chloride solution. The organic phase is dried over magnesium sulfate, filtered and concentrated under reduced pressure, and the resulting solid is then taken up in diethyl ether/acetonitrile, stirred for 30 min and subsequently filtered. 53.0 mg (44% of theory) of the title compound are obtained.

$^1$H-NMR (400 MHz, DMSO-$d_6$): δ=8.81 (s, 0.6H), 8.71 (s, 0.4H), 7.60-7.33 (m, 8H), 5.50 (s, 0.8H), 4.94 (s, 1.2H), 4.60 (s, 1.2H), 4.03 (s, 0.8H).

LC-MS (Method 12): $R_t$=1.18 min; MS (ESIpos): m/z=418 [M+H]$^+$.

Example 21

3-{4-(3-Chlorophenyl)-2-[(4-oxoimidazolidin-1-yl) carbonyl]-1,3-thiazol-5-yl}-5-fluorobenzenecarbonitrile

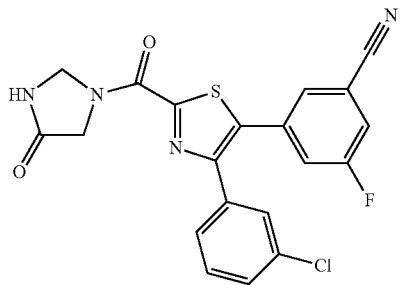 [SMILES: N#Cc1cc(F)cc(-c2sc(C(=O)N3CNC(=O)C3)nc2-c2cccc(Cl)c2)c1]

90.0 mg of the compound from Example 40A having a purity of 90% (0.226 mmol), 49.7 mg (0.248 mmol) of the compound from Example 20A and 176 mg (0.339 mmol) of PyBOP are provided in 5.0 ml of tetrahydrofuran, and 126 μl (0.722 mmol) of N,N-diisopropylethylamine are added at room temperature. The reaction solution is stirred at room temperature overnight, diluted with dichloromethane and subsequently washed with a 1N aqueous hydrogen chloride solution. The organic phase is dried over magnesium sulfate, filtered and concentrated under reduced pressure, and the crude product is then purified by preparative HPLC (RP18 column; mobile phase: acetonitrile/water gradient). 62.0 mg (64% of theory) of the title compound are obtained.

$^1$H-NMR (400 MHz, DMSO-$d_6$): δ=8.81 (s, 0.6H), 8.71 (s, 0.4H), 8.00 (d, 1H), 7.85 (br. s., 1H), 7.72 (d, 1H), 7.58 (br. s., 1H), 7.53-7.46 (m, 1H), 7.45-7.38 (m, 1H), 7.38-7.30 (m, 1H), 5.50 (s, 0.8H), 4.95 (s, 1.2H), 4.60 (s, 1.2H), 4.03 (s, 0.8H).

LC-MS (Method 7): $R_t$=1.89 min; MS (ESIpos): m/z=427 [M+H]$^+$.

B) Assessment of the Physiological Activity

Abbreviations:
DMSO dimethyl sulfoxide
FCS fetal calf serum (Biochrom AG, Berlin, Germany)
PBS phosphate buffered saline
MTP microtiter plate
ELISA enzyme-linked immunosorbent assay The suitability of the compounds of the invention for the treatment of diseases caused by retroviruses can be shown in the following assay systems:

In Vitro Assays

Biochemical Reverse Transcriptase Assay

The "Reverse Transcriptase Assay, colorimetric" (Roche Diagnostics GmbH, Mannheim, Germany) is used in accordance with the manufacturer's information. The test substances are dissolved in DMSO and are used in the test diluted in 5-fold steps (final DMSO concentration 1%). The resulting values of the photometric evaluation (405/492 nm) are less than 0.1 for the negative control (mixture without reverse transcriptase) and are in the region of 1.5 for the positive control (mixture without test substance). The $IC_{50}$ values of the test substances are determined as the concentration of the test substance dilution at which the measured optical density is 50% of the positive control.

It is found that the compounds of the invention inhibit the reverse transcriptase activity. Experimental data are summarized in Table A.

Light Assay with Wild-Type and Inhibitor-Resistant HI Reporter Viruses

HIV-1$_{NL4-3}$ reporter viruses which carry the lu164 gene (luciferase 164) instead of the nef gene are used for this assay. The viruses are generated by transfection of 293T cells with the corresponding proviral pNL4-3 plasmid (Lipofectamine Reagent, Invitrogen, Karlsruhe, Germany). Starting from the proviral plasmid DNA using the "QuikChange II XL Site-Directed Mutagenesis Kit" (Stratagene, Cedar Creek, Tex., USA) viruses with defined resistance mutations in the reverse transcriptase gene are produced. The following mutations, inter alia, are generated: A98G, A98G-K103N-V108I, A98S, F227C, F227L, G190A, G190S, K101E, K101Q-K103N, K103N, K103N-F227L, K103N-G190A, K103N-G190S, K103N-M230L, K103N-N348I, K103N-P225H, K103N-V108I, K103N-V108I-P225H, K103N-V179F-Y181C, K103N-Y181C, K103N-Y181C-G190A, L100I, L100I-K103N, L100I-K103N-V179I-Y181C, L100I-K103N-Y181C, L234I, N348I, P225H, P236L, V106A, V106A-E138K, V106A-F227C, V106A-F227L, V106I, V106I-Y188L, V106M, V108I, V179F-Y181C, V179I, V179I-Y181C, Y181C, Y181C-G190A, Y181C-M230L, Y181I, Y188L. MT4 7F2 cells infected with these reporter viruses secrete luciferase into the medium, thus enabling virus replication to be quantified by luminometry.

For the mixture for a 96-well MTP, 3 million MT4 7F2 cells are pelleted, suspended in 1 ml of RPMI 1640 medium without phenol red (Invitrogen, Karlsruhe, Germany)/10% FCS/10% AIM-V (Invitrogen, Karlsruhe, Germany) and incubated together with a suitable amount of the corresponding HIV-1$_{NL4-3}$ reporter virus at 37° C. for 2 hours (pellet infection). Unadsorbed viruses are subsequently washed out with PBS, and the infected cells are pelleted again and suspended in 8 ml of RPMI 1640 medium without phenol red/2% or 10% FCS/10% AIM-V. 80 μl thereof are pipetted into each well of a white 96-well MTP with 20 μl of test substance in suitable dilution. To avoid edge effects, the wells on the edge of the MTP are not used for substance dilutions. The second vertical row of the MTP contains only infected cells (virus control) and the eleventh vertical row only uninfected cells (cell control), in each case in RPMI 1640 medium without phenol red/2% or 10% FCS/10% AIM-V. The other wells of the MTP contain the compounds of the invention in various concentrations starting from the third vertical row, from which the test substances are diluted in 3-fold steps up to the tenth vertical row 3$^7$-fold. The test substances are dissolved in DMSO, whereby the final DMSO concentration in the test mixture is 1%. The test mixtures are incubated at 37° C./5% $CO_2$ for five days and, after the addition of 15 μl of Lu164 substrate (5 mg/ml coelenterazine dissolved in 30 μM glutathione/DMSO, 100 mM NaCl, 1M MES, 100 mM glutathione), evaluated by luminometry. The resulting values are in the region of 1 000 000 RLUs (relative light units) for the virus control and 300 to 400 RLUs for the cell control. The $EC_{50}$ values of the test substances are determined as the concentration at which the virus replication measured in RLUs is 50% of the untreated infected cells.

It is found that the compounds of the invention inhibit the HIV replication. Experimental data are summarized in Table A.

PBL and H9 Assay with Wild-Type HIV-1

Primary human blood lymphocycles (PBLs) are isolated from blood using Ficoll-Paque Leucosep tubes (Greiner Bio-One, Frickenhausen, Germany) and stimulated with phytohaemagglutinin (90 µg/ml) and interleukin-2 (40 U/ml) in RPMI 1640 medium (Invitrogen, Karlsruhe, Germany)/10% FCS for 3 days.

For the mixture for a 96-well MTP, 3 million PBLs are pelleted, suspended in 1 ml of RPMI 1640 medium/10% FCS and incubated together with a suitable amount of HIV-1$_{LAI}$ (NIH AIDS Research & Reference Reagent Program, Germantown, USA) at 37° C. for 2 hours (pellet infection). Unadsorbed viruses are subsequently washed out with PBS, and the infected cells are pelleted again and suspended in 18 ml of RPMI 1640 medium/10% FCS/interleukin-2 (40 U/ml). 180 µl thereof are pipetted into each well of a white 96-well MTP with 20 µl of test substance in suitable dilution. Alternatively, after preparation of the substance dilutions in the MTP, the HIV is pipetted in together with the cells and is not washed out again (supernatant infection). In order to avoid edge effects, the wells at the edge of the MTP are not used for substance dilutions. The second vertical row of the MTP contains only infected cells (virus control) and the eleventh vertical row only uninfected cells (cell control), in each case in RPMI 1640 medium/10% FCS/interleukin-2 (40 U/ml). The other wells of the MTP contain the compounds of the invention in various concentrations starting from the third vertical row, from which the test substances are diluted in 3-fold steps up to the tenth vertical row $3^7$-fold. The test substances are dissolved in DMSO, whereby the final DMSO concentration in the test mixture is 1%. The test mixtures are incubated at 37° C./5% $CO_2$. After 5 and 7 days, 50 µl of cell-free supernatant are removed from each well to determine the amount of p24 present by means of a p24 ELISA (HIV-1 p24$^{CA}$ Antigen Capture Assay Kit, NCI-Frederick Cancer Research and Development Center, Frederick, USA). From the resulting values of the photometric evaluation (450/620 nm) the $EC_{50}$ values of the test substances are determined as the concentration at which the amount of p24 is 50% of the untreated infected cells.

Alternatively, H9 cells (ATCC, Wesel, Germany) are employed instead of PBLs for testing the test substances. H9 cells are incubated in RPMI 1640 medium with 2% or 10% FCS as a HIV-1$_{LAI}$ supernatant infection at 37° C./5% $CO_2$, (20 µl of substance dilution and 80 µl of cells/virus per well) in accordance with the pattern described above for 5 days. Subsequently, 10 µl of AlamarBlue (Invitrogen, Karlsruhe, Germany) are added to each well, and the MTPs are incubated at 37° C. for 3 hours before the fluorimetric evaluation takes place (544/590 nm). The resulting values are about 40 000 for the untreated uninfected cells and about 7000 for the untreated infected cells. In the low concentration range, the $EC_{50}$ values of the test substances are determined as the concentration at which the fluorescence is 50% of the untreated uninfected cells (in each case subtracting the values of the untreated infected cells). In addition, in the high concentration range, the $CC_{50}$ values of the test substances are determined as the concentration at which the fluorescence is 50% of the untreated uninfected cells (in each case subtracting the values of the untreated infected cells).

It is found that the compounds of the invention inhibit the HIV replication. Experimental data are summarized in Table A.

Assay to Determine the Cytotoxic Effect of the Test Substances

To determine the cytotoxic effect of the test substances in uninfected cells, the substances are pipetted in appropriate concentrations into transparent 96-well MTPs and incubated with uninfected cells (e.g. H9, PBLs, THP-1, MT4 7F2, CEM, Jurkat) (in analogy to the assays described above). After 5 days, per each well 1/10 of the volume AlamarBlue is added to the test mixtures, and the MTPs are incubated at 37° C. for 3 hours. The fluorimetric evaluation (544/590 nm) subsequently takes place. The resulting values are between 20 000 and 40 000 for untreated cells, depending on the type of cell. The $CC_{50}$ values of the test substances are determined as the concentration at which the fluorescence is 50% of the untreated cells. Test substances which show cytotoxic findings in the concentration range of the effect are not evaluated for their antiviral activity.

TABLE A

| Example No. | $IC_{50}$ (nM) RT assay | $EC_{50}$ (nM) H9 cells HIV-1$_{LAI}$ 10% FCS | $EC_{50}$ (nM) MT4 7F2 cells HIV-1$_{NLA-M3}$ wt 2% FCS | $EC_{50}$ (nM) MT4 7F2 cells HIV-1$_{NLA-M3}$ K103N-Y181C 2% FCS |
|---|---|---|---|---|
| Example 1 | 61 | 14 | 2 | 55 |
| Example 2 | 17 | 30 | 4 | 91 |
| Example 3 | 20 | 12 | 0.6 | 60 |
| Example 4 |  | 80 | 10 | 143 |
| Example 5 |  | 80 | 38 | 228 |
| Example 6 |  | 95 | 58 | 282 |
| Example 7 |  | 20 | 36 | 303 |
| Example 8 |  |  | 46 | 142 |
| Example 9 |  | 40 | 35 | 118 |
| Example 10 |  | 5 | 4 | 70 |
| Example 11 | 13 | 4 | 5 | 69 |
| Example 12 |  | 80 | 29 | 119 |
| Example 13 |  | 2 | 0.6 | 43 |
| Example 14 |  | 4 | 1 | 49 |
| Example 15 |  | 2 | 9 | 87 |
| Example 16 |  | 2 | 15 | 123 |
| Example 17 |  | 2 | 0.5 | 64 |
| Example 18 |  | 1 | 0.4 | 38 |
| Example 19 |  | 1 | 2 | 94 |
| Example 20 | 47 | 7 | 1 | 149 |
| Example 21 |  | 2 | 2 | 79 |

In Vivo Assay

Animal Model:

NOD SCID mice, usually 5-6 weeks old, are purchased from commercial breeders (e.g. Taconic or Jackson Laboratory). The animals are kept under sterile conditions (including bedding and feed) in isolators.

A defined number of cells (e.g. $5 \times 10^6$ T cells (e.g. C8166)) is infected with HIV with a suitable m.o.i. (e.g. 0.01 TCID$^{50}$). The infected cells are introduced into collagen sponges. The sponges pretreated in this way are implanted under the dorsal skin of the mice. The mice are treated once or several times each day orally, intraperitoneally, subcutaneously or intravenously, whereby it is possible that the first treatment takes place before the implantation. The treatment groups usually include 10 mice. At least one group is treated with placebo, at least one group with a substance known to be active (=positive control) and usually several groups with the substance of the invention. The daily dose of the substance of the invention is between 0.01 mg and 100 mg per kg of body weight. The substances are formulated in 2% DMSO/0.5% methylcellulose in PBS or another suitable mixture which assists the solubility of the substances. The treatment usually lasts four and a half days. After the last administration of the substance, the animals are sacrificed and the sponges are removed. The virus-infected cells are obtained from the sponge by collagenase digestion.

The total RNA is obtained from the cells and is examined by quantitative PCR for the content of viral RNA. The amount of viral RNA is normalized on the basis of the amount of a housekeeping gene (e.g. GAPDH). The amount of HIV RNA after treatment with the substance compared with the placebo-treated control group is determined. If an HIV carrying a luciferase was used it is possible in addition or as substitute to carry out a luciferase measurement. In this case, the amount of HIV is determined from the level of the luciferase signal because it serves as a measure of the viral replication in this case. Statistical analysis takes place by means of suitable computer programs, e.g. Graph Pad Prism.

B) Assessment of the Pharmacokinetic Properties

In Vivo Studies

To determine the in vivo pharmacokinetics, the test substances are administered intravenously and orally to mice, rats and dogs. The dose chosen in intravenous studies for determining the pharmacokinetic properties of the test substances is 0.5 mg/kg in all species. On oral administration, 3 mg/kg is administered to the rodents, and 1 mg/kg to dogs. The test substances are formulated in 99% plasma, 1% DMSO for the intravenous administration for rodents, and in PEG 400, ethanol and water in varying proportions for oral administration. The latter vehicle is used for both administration routes for dogs.

Male Wistar rats are catheterized before the administration of the test substances so that the blood samples can be taken with the aid of the catheter in place or by puncture of the vena cava at various times over an interval of from 2 min up to 26 h.

The test substances are administered to female BalbC mice intravenously as bolus injection, and in this case samples are obtained exclusively by puncture of the vena cava over an interval of from 2 min up to 26 h. Administration to female beagle dogs exclusively takes place by a 15-minute intravenous infusion. The samples are obtained by puncture of the brachial vein or the jugular vein over an interval of from 10 min up to 26 h.

The substances are quantitatively determined from the animal plasma obtained and calibration samples adjusted in plasma. The plasma proteins are removed by precipitation with acetonitrile (ACN). The samples are subsequently fractionated by HPLC on an Agilent 1100 LC system (Agilent, Santa Clara, Calif., USA) using various columns, e.g. Luna C8, LichroCart Purospher Star RP18e. The HPLC system is coupled via a Turbo Ion Spray interface to an API 3000 triple quadropole mass spectrometer (Applied Biosystems, Darmstadt, Germany). The evaluation of the plasma concentration-time course takes place by employing an internal standard and using a validated kinetic analysis program.

Besides studies to determine the pharmacokinetic parameters of the test substances in vivo, determinations of the relative bioavailability from suspension (formulation: Tylose suspension) versus solution in the rat as well as high-dose studies preliminary to tests of effect and toxicological studies in mice, rats and dogs are carried out.

Plasma Stability

The plasma used from the various species (BalbC mouse, Wistar rat, beagle dog and human) is obtained fresh by taking blood into monovettes coated with Li-heparin and subsequent centrifugation. In order to determine the plasma stability of the test substances 2 ml containing in each case 500 ng/ml in plasma are incubated at 37° C. Samples are taken from the incubation vessel at various times over an interval of up to 3 h. The samples obtained are precipitated with ACN in order to stop the reaction and remove the plasma proteins. The samples are analysed in a manner equivalent to the in vivo studies.

Microsomal and Hepatocyte Incubations

Incubations with liver microsomes of various species (BalbC mouse, Wistar rat, beagle dog, human) are carried out in a total volume of 1.5 ml at 37° C. in a modified Multiprobe II® robot system (Canberra Packard) or Janus® robot system (Perkin Elmer).

The incubation mixtures each comprise 0.5 µg/ml test substance as well as 0.2-0.5 mg/ml microsomal protein. In addition, 0.05 M phosphate buffer (pH=7.4), 1 mM EDTA, 5 mM glucose 6-phosphate and 1.5 U/ml glucose-6-phosphate dehydroxygenase from *Leuconostoc Mesenteroides* are added. The microsomal incubation is started by adding NADP$^+$ (final concentration: 1 mM).

In each case 1 million cells/ml are used to determine the metabolic stability of the test substances in freshly isolated and cultivated rat, dog and human hepatocytes. In a manner equivalent to the microsomal assay, in each case 0.5 µg/ml test substance are added to the hepatocytes.

125 µl are removed from the respective incubation mixture after 2, 5, 10, 20, 30, 45 and 60 min, or after 2, 10, 20, 30, 50, 70 and 90 min for more stable compounds, and ACN is added in order to stop the enzymatic reactions. After centrifugation, the samples are analysed by LC-MS/MS (API 2000 or 3000, Applied Biosystems). "CL$_{blood}$ well-stirred" and "F$_{max}$ well-stirred" values are calculated from the respective half-lives of the compounds in the microsomal incubations. The substrate degradation can be described by the following formulae (Houston J B, Utility of in-vitro drug-metabolism data in predicting in-vivo metabolic-clearance, Bioch. Pharm. 47 (9) 1469-1479 (1994); Obach R S; Baxter J G; Liston T E; Silber B M; Jones B C; MacIntyre F; Rance D J; Wastall P, The prediction of human pharmacokinetic parameters from preclinical and in vitro metabolism data, J. Pharmacol. Exp. Ther. 283 (1) 46-58 (1997)): CL$'_{intrinsic}$ [ml/(min·kg)]= (0.693/in vitro t$_{1/2}$ [min])·(liver weight [g liver/kg body weight])·(microsomal protein [mg]/liver weight [g])/(microsomal protein [mg]/incubation volume [ml]).

The blood clearance "CL$_{blood}$" is described by the "well-stirred" model, ignoring protein bindings (Pang K S; Rowland M, Hepatic clearance of drugs. I. Theoretical considerations of a "well-stirred" model and a "parallel tube" model. Influence of hepatic blood flow, plasma and blood cell binding, and the hepatocellular enzymatic activity on hepatic drug clearance, J Pharmacokinet Biopharm 5 (6): 625-53 (1977)):

$$CL_{blood} \text{ well-stirred } [l/(h \cdot kg)] = (Q_H[l/(h \cdot kg)] \cdot CL'_{intrinsic} [l/(h \cdot kg)])/(Q_H[l/(h \cdot kg)] + CL'_{intrinsic}[l/(h \cdot kg)]).$$

For rats, the specific liver weight is 32 g/kg of body weight and the hepatic blood flow is 4.2 l/(h·kg). The specific microsomal protein content of the rat liver was estimated at 40 mg/g of liver. The specific extrapolation factors for further species are shown in the following table and are based in part on literature data and in part on our own determinations. For hepatocytes a cell count of 110 million/g of liver is used for the calculation for all species.

|  | Mouse m | Mouse f | Rat m | Dog m/f | Human m/f |
| --- | --- | --- | --- | --- | --- |
| Microsomal protein/g of liver [mg] | 40 | 40 | 40 | 40 | 40 |
| Liver [g]/kg of body weight | 50 | 43 | 32 | 39 | 21 |
| Liver blood flow [l/(h·kg)] | 5.4 | 5.4 | 4.2 | 2.1 | 1.32 |

C) Exemplary Embodiments of Pharmaceutical Compositions

The compounds of the invention can be converted into pharmaceutical preparations in the following ways:

Tablet:

Composition:

100 mg of the compound of Example 1, 50 mg of lactose (monohydrate), 50 mg of corn starch (native), 10 mg of polyvinylpyrrolidone (PVP 25) (BASF, Ludwigshafen, Germany) and 2 mg of magnesium stearate.

Tablet weight 212 mg, diameter 8 mm, radius of curvature 12 mm.

Production:

The mixture of compound of the invention, lactose and starch is granulated with a 5% solution (m/m) of the PVP in water. The granules are mixed with the magnesium stearate for 5 minutes after drying. This mixture is compressed with a conventional tablet press (see above for format of the tablet). A guideline compressive force for the compression is 15 kN.

Solution which can be Administered Orally:

Composition:

500 mg of the compound of Example 1, 2.5 g of polysorbate and 97 g of polyethylene glycol 400.20 g of oral solution correspond to a single dose of 100 mg of the compound of the invention.

Production:

The compound of the invention is suspended in the mixture of polyethylene glycol and polysorbate with stirring. The stirring process is continued until the compound of the invention has completely dissolved.

i.v. Solution:

The compound of the invention is dissolved in a concentration below the saturation solubility in a physiologically tolerated solvent (e.g. isotonic saline solution, 5% glucose solution, 30% PEG 400 solution). The solution is sterilized by filtration and dispensed into sterile and pyrogen-free injection containers.

What is claimed is:

1. A compound of formula (I)

in which $R^1$ represents phenyl, whereby phenyl is substituted with 1 to 3 substituents, whereby the substituents are selected independently of one another from the group consisting of halogen, hydroxy, cyano, nitro, trifluoromethyl, trifluoromethoxy, trifluoromethylthio, $(C_1\text{-}C_4)$-alkyl and $(C_1\text{-}C_4)$-alkoxy, wherein $(C_1\text{-}C_4)$-alkyl and $(C_1\text{-}C_4)$-alkoxy in turn may be substituted one to three times identically or differently with radicals selected from the group consisting of halogen, cyano, hydroxy, $(C_1\text{-}C_4)$-alkoxy, amino, mono-$(C_1\text{-}C_4)$-alkylamino, di-$(C_1\text{-}C_4)$-alkylamino, $(C_3\text{-}C_7)$-cycloalkyl and 4- to 7-membered heterocyclyl, whereby the last-mentioned cycloalkyl and heterocyclyl radicals in turn may each be substituted up to three times identically or differently with halogen, cyano, $(C_1\text{-}C_4)$-alkyl, trifluoromethyl, hydroxy, $(C_1\text{-}C_4)$-alkoxy, trifluoromethoxy, oxo, amino, mono-$(C_1\text{-}C_4)$-alkylamino and di-$(C_1\text{-}C_4)$-alkylamino, and $R^2$ represents phenyl, whereby phenyl is substituted with 1 to 3 substituents, whereby the substituents are selected independently of one another from the group consisting of halogen, hydroxy, cyano, nitro, trifluoromethyl, trifluoromethoxy, trifluoromethylthio, $(C_1\text{-}C_4)$-alkyl and $(C_1\text{-}C_4)$-alkoxy, wherein $(C_1\text{-}C_4)$-alkyl and $(C_1\text{-}C_4)$-alkoxy in turn may be substituted one to three times identically or differently with radicals selected from the group consisting of halogen, cyano, hydroxy, $(C_1\text{-}C_4)$-alkoxy, amino, mono-$(C_1\text{-}C_4)$-alkylamino, di-$(C_1\text{-}C_4)$-alkylamino, $(C_3\text{-}C_7)$-cycloalkyl and 4- to 7-membered heterocyclyl, whereby the last-mentioned cycloalkyl and heterocyclyl radicals in turn may each be substituted up to three times identically or differently with halogen, cyano, $(C_1\text{-}C_4)$-alkyl, trifluoromethyl, hydroxy, $(C_1\text{-}C_4)$-alkoxy, trifluoromethoxy, oxo, amino, mono-$(C_1\text{-}C_4)$-alkylamino and di-$(C_1\text{-}C_4)$-alkylamino, or one of the salts thereof.

2. The compound of claim 1, whereby $R^1$ represents phenyl, whereby phenyl is substituted with 1 to 2 substituents, whereby the substituents are selected independently of one another from the group consisting of halogen, hydroxy, cyano, nitro, trifluoromethyl, trifluoromethoxy, trifluoromethylthio, $(C_1\text{-}C_4)$-alkyl and $(C_1\text{-}C_4)$-alkoxy, and $R^2$ represents phenyl, whereby phenyl is substituted with 1 to 2 substituents, whereby the substituents are selected independently of one another from the group consisting of halogen, hydroxy, cyano, nitro, trifluoromethyl, trifluoromethoxy, trifluoromethylthio, $(C_1\text{-}C_4)$-alkyl and $(C_1\text{-}C_4)$-alkoxy, wherein $(C_1\text{-}C_4)$-alkoxy in turn may be substituted one or three times identically or differently with radicals selected from the group consisting of halogen, cyano, hydroxy, $(C_1\text{-}C_4)$-alkoxy, amino, mono-$(C_1\text{-}C_4)$-alkylamino, di-$(C_1\text{-}C_4)$-alkylamino, $(C_3\text{-}C_7)$-cycloalkyl and 4- to 7-membered heterocyclyl, whereby the last-mentioned cycloalkyl and heterocyclyl radicals in turn may each be substituted up to three times identically or differently with halogen, cyano, $(C_1\text{-}C_4)$- alkyl, trifluoromethyl, hydroxy, $(C_1$-$C_4)$-alkoxy, trifluoromethoxy, oxo, amino, mono-$(C_1$-$C_4)$-alkylamino and di-$(C_1$-$C_4)$-alkylamino, and or one of the salts thereof.

3. The compound of claim 1, whereby $R^1$ represents phenyl, whereby phenyl is substituted with 1 to 2 substituents, whereby the substituents are selected independently of one another from the group consisting of halogen, cyano, trifluoromethyl, methyl and methoxy, and $R^2$ represents phenyl, whereby phenyl is substituted with 1 to 2 substituents, where the substituents are selected independently of one another from the group consisting of halogen, cyano, trifluoromethyl, trifluoromethoxy, methyl and $(C_1$-$C_3)$-alkoxy, or one of the salts thereof.

4. The compound of claim 1, corresponding to formula

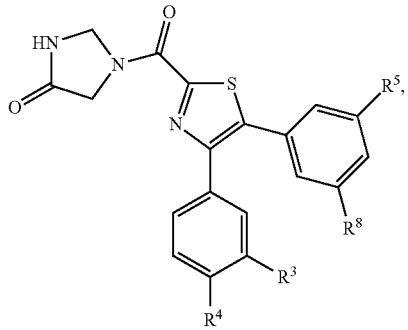

(Ia)

in which $R^3$ represents halogen or cyano, $R^4$ represents hydrogen or halogen, $R^5$ represents halogen, cyano or trifluoromethyl, and $R^6$ represents hydrogen or halogen, or one of the salts thereof.

5. The compound of claim 4, whereby $R^3$ represents fluorine, chlorine or cyano, $R^4$ represents hydrogen, chlorine or fluorine, $R^5$ represents fluorine, chlorine or cyano, and $R^6$ represents hydrogen, chlorine or fluorine, or one of the salts thereof.

6. The compound of claim 4, whereby $R^3$ represents chlorine or cyano, $R^4$ represents hydrogen or fluorine, $R^5$ represents halogen or cyano, and $R^6$ represents hydrogen or fluorine, or one of the salts thereof.

7. A method for preparing a compound of formula (I) of claim 1, comprising reacting a compound of formula

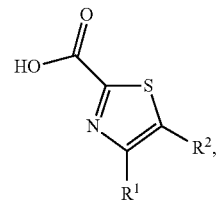

(II)

in which $R^1$ and $R^2$ have the meaning given in claim 1, with imidazolidin-4-one or a salt of imidazolidin-4-one.

8. A method for preparing a compound of formula (I) of claim 1, comprising reacting a compound of formula

(VII)

in which $R^1$ has the meaning given in claim 1, under Suzuki coupling conditions with a compound of formula $R^2$-Q     (IV), in which $R^2$ has the meaning given in claim 1 and Q represents —$B(OH)_2$, a boronic acid ester, a boronic acid pinacol ester, or —$BF_3^-K^+$.

9. A method for the manufacture of a medicament comprising mixing a compound of claim 1 with at least one inert, non-toxic, pharmaceutically acceptable excipient.

10. A medicament comprising a therapeutically effective amount of at least one compound of claim 1 in combination with at least one further active compound.

11. A medicament comprising a therapeutically effective amount of at least one compound of claim 1 in combination with at least one inert, non-toxic, pharmaceutically acceptable excipient.

12. A method for treating HIV in humans and animals comprising administering an antivirally effective amount of at least one compound of claim 1 to a human or animal in need thereof.

13. A method for treating HIV in humans and animals comprising administering an antivirally effective amount of a medicament of claim 10 to a human or animal in need thereof.

14. A method for treating HIV in humans and animals comprising administering an antivirally effective amount of a medicament of claim 11 to a human or animal in need thereof.

* * * * *